US011633367B2

(12) United States Patent
Emgenbroich et al.

(10) Patent No.: US 11,633,367 B2
(45) Date of Patent: Apr. 25, 2023

(54) TRANSDERMAL DELIVERY SYSTEM CONTAINING ROTIGOTINE

(71) Applicant: LTS Lohmann Therapie-Systeme AG, Andernach (DE)

(72) Inventors: Marco Emgenbroich, Rheinbach (DE); Elke Klein, Bad Neuenahr-Ahrweiler (DE); Heike Kluth, Ochtendung (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 15/312,509

(22) PCT Filed: May 20, 2015

(86) PCT No.: PCT/EP2015/061099
§ 371 (c)(1),
(2) Date: Nov. 18, 2016

(87) PCT Pub. No.: WO2015/177204
PCT Pub. Date: Nov. 26, 2015

(65) Prior Publication Data
US 2017/0105945 A1    Apr. 20, 2017

(30) Foreign Application Priority Data
May 20, 2014  (EP) .................................. 14169009

(51) Int. Cl.
*A61K 9/70*     (2006.01)
*A61K 31/381*   (2006.01)
*A61K 9/00*     (2006.01)

(52) U.S. Cl.
CPC .......... *A61K 9/7069* (2013.01); *A61K 9/0014* (2013.01); *A61K 9/7053* (2013.01); *A61K 9/7061* (2013.01); *A61K 9/7084* (2013.01); *A61K 9/7092* (2013.01); *A61K 31/381* (2013.01)

(58) Field of Classification Search
None
See application file for complete search history.

(56) References Cited

U.S. PATENT DOCUMENTS

| | | | |
|---|---|---|---|
| 4,769,028 A | 9/1988 | Hoffman et al. | |
| 4,814,168 A | 3/1989 | Sablotsky et al. | |
| 4,994,267 A | 2/1991 | Sablotsky | |
| 4,994,278 A | 2/1991 | Sablotsky et al. | |
| 5,032,207 A | 7/1991 | Sablotsky et al. | |
| 5,300,291 A | 4/1994 | Sablotsky et al. | |
| 5,405,486 A | 4/1995 | Sablotsky et al. | |
| 5,474,783 A | 12/1995 | Miranda et al. | |
| 5,656,285 A | 8/1997 | Sablotsky et al. | |
| 5,656,286 A | 8/1997 | Miranda et al. | |
| 5,686,099 A | 11/1997 | Sablotsky et al. | |
| 5,719,197 A | 2/1998 | Kanios et al. | |
| 5,958,446 A | 9/1999 | Miranda et al. | |
| 6,024,976 A | 2/2000 | Miranda et al. | |
| 6,221,383 B1 | 4/2001 | Miranda et al. | |
| 6,235,306 B1 | 5/2001 | Miranda et al. | |
| 6,884,434 B1 | 4/2005 | Müller et al. | |
| 7,383,083 B2 | 6/2008 | Fischer et al. | |
| 7,847,014 B2 | 12/2010 | Koch et al. | |
| 8,211,462 B2 | 7/2012 | Breitenbach et al. | |
| 8,246,979 B2 * | 8/2012 | Schacht | A61K 9/7061 424/443 |
| 9,265,752 B2 * | 2/2016 | Wang | A61K 9/7053 |
| 2001/0053383 A1 | 12/2001 | Miranda et al. | |
| 2003/0026830 A1 | 2/2003 | Lauterback et al. | |
| 2003/0060479 A1 | 3/2003 | Brown et al. | |
| 2003/0149394 A1 | 7/2003 | Joshi | |
| 2003/0198622 A1 | 10/2003 | Gaiger | |

(Continued)

FOREIGN PATENT DOCUMENTS

CA    2374930 A1    1/2001
CN    1462185 A    12/2003
(Continued)

OTHER PUBLICATIONS

International Search Report issued in corresponding International Application No. PCT/EP2015/061099.
Office Actions in U.S. Appl. No. 14/443,210, dated Nov. 28, 2016; May 4, 2017; Dec. 11, 2017; Oct. 16, 2018; and Mar. 18, 2019.
Office Actions in U.S. Appl. No. 16/009,613, dated Mar. 24, 2017 and Oct. 5, 2017. (parent to U.S. Appl. No. 16/009,613).
Office Action in U.S. Appl. No. 15/312,433, dated Jul. 18, 2019.
Office Actions in U.S. Appl. No. 15/312,542, dated Dec. 22, 2017, Jul. 17, 2018, Dec. 27, 2018 and Jun. 18, 2019.
Office Actions in U.S. Appl. No. 16/009,613, dated Dec. 20, 2018.
International Preliminary Report on Patentability, PCT/EP2013/003515, which corresponds to U.S. Appl. No. 14/443,210, filed May 15, 2015.
International Search Report, PCT/EP2013/003515, which corresponds to U.S. Appl. No. 14/443,210, filed May 15, 2015.

(Continued)

*Primary Examiner* — David J Blanchard
*Assistant Examiner* — Daniel F Coughlin
(74) *Attorney, Agent, or Firm* — ProPat, LLC; Cathy Moore

(57) ABSTRACT

A transdermal therapeutic system containing rotigotine base in a self-adhesive layer structure. The system includes a backing layer, and a rotigotine-containing biphasic layer. The biphasic layer has an outer phase having a composition including 75% to 100% of a polymer or a polymer mixture, and an inner phase that forms dispersed deposits in the outer phase. The inner phase includes rotigotine base and a polymer mixture of at least two hydrophilic polymers. The hydrophilic polymers are selected from the group of polyvinylpyrrolidones having a K-Value of at least 80, polyvinylpyrrolidones having a K-Value of less than 80, copolymers of vinyl caprolactam, vinylacetate and ethylene glycol, copolymers of vinylpyrrolidone and vinylacetate, copolymers of ethylene and vinylacetate, polyethylene glycols, polypropylene glycols, acrylic polymers, and modified celluloses. The polymer mixture in the inner phase is present in an amount sufficient so that it forms a solid solution with the rotigotine base.

38 Claims, 3 Drawing Sheets

(56) References Cited

U.S. PATENT DOCUMENTS

| | | | |
|---|---|---|---|
| 2004/0131897 A1 | 7/2004 | Jenson et al. | |
| 2004/0137045 A1 | 7/2004 | Breitenbach et al. | |
| 2004/0138299 A1* | 7/2004 | Cahill | A61K 9/146 |
| | | | 514/521 |
| 2004/0234583 A1 | 11/2004 | Müller | |
| 2005/0019385 A1 | 1/2005 | Houze | |
| 2005/0175678 A1 | 8/2005 | Breitenbach | |
| 2005/0202073 A1 | 9/2005 | Jackson et al. | |
| 2005/0260254 A1 | 11/2005 | Breitenbach et al. | |
| 2006/0263419 A1 | 11/2006 | Wolff | |
| 2009/0048556 A1 | 2/2009 | Durand | |
| 2009/0299304 A1 | 12/2009 | Tang | |
| 2010/0119585 A1 | 5/2010 | Hille et al. | |
| 2010/0286590 A1 | 11/2010 | Durand | |
| 2010/0311661 A1 | 12/2010 | Küllertz et al. | |
| 2011/0027345 A1 | 2/2011 | Wang et al. | |
| 2011/0104244 A1 | 5/2011 | Hille | |
| 2014/0046279 A1 | 2/2014 | Leonhard et al. | |
| 2015/0290142 A1* | 10/2015 | Cawello | A61P 21/00 |
| | | | 604/307 |

FOREIGN PATENT DOCUMENTS

| | | | |
|---|---|---|---|
| CN | 1606435 A | | 4/2005 |
| CN | 1671375 A | | 9/2005 |
| CN | 101146524 A | | 3/2008 |
| CN | 101601664 A | | 12/2009 |
| CN | 1897935 A | | 5/2010 |
| CN | 102458397 A | | 5/2012 |
| CN | 102770128 A | | 11/2012 |
| DE | 10 2012 013 421 | | 1/2014 |
| EP | 1 669 063 A1 | | 6/2006 |
| EP | 2 177 217 A1 | | 4/2010 |
| EP | 2 292 219 A1 | | 3/2011 |
| JP | 1998509621 A | | 9/1998 |
| JP | 2003-526656 A | | 9/2003 |
| JP | 2004-521085 A | | 7/2004 |
| JP | 2004525164 A | | 8/2004 |
| JP | 2004528359 A | | 9/2004 |
| JP | 2005-528425 A | | 9/2005 |
| JP | 2005-535686 A | | 11/2005 |
| JP | 2005535687 A | | 11/2005 |
| JP | 2006-508908 A | | 3/2006 |
| JP | 2006515952 A | | 6/2006 |
| JP | 2006178807 A | | 7/2006 |
| JP | 2007-528392 A | | 10/2007 |
| JP | 2009297808 A | | 12/2009 |
| JP | 2010-106037 A | | 5/2010 |
| JP | 2010158554 A | | 7/2010 |
| JP | 2010536434 A | | 12/2010 |
| JP | 2011500647 A | | 1/2011 |
| JP | 2011-504902 A | | 2/2011 |
| JP | 2011526592 A | | 10/2011 |
| JP | 2012501799 A | | 1/2012 |
| JP | 2012-504609 A | | 2/2012 |
| JP | 2012-509276 A | | 4/2012 |
| JP | 2013510805 A | | 3/2013 |
| JP | 2013-515041 A | | 5/2013 |
| WO | 89/10108 A1 | | 11/1989 |
| WO | 91/14463 A1 | | 10/1991 |
| WO | WO 91/14463 | | 10/1991 |
| WO | 92/19451 A1 | | 11/1992 |
| WO | WO 92/19451 | | 11/1992 |
| WO | 93/00058 A1 | | 1/1993 |
| WO | WO 93/00058 | | 1/1993 |
| WO | 95/18603 A1 | | 7/1995 |
| WO | WO 95/18603 | | 7/1995 |
| WO | 99/49852 A1 | | 10/1999 |
| WO | 2000/44437 A1 | | 8/2000 |
| WO | 2001/01967 A1 | | 1/2001 |
| WO | 2002/015903 A2 | | 2/2002 |
| WO | WO 2002/089777 | | 11/2002 |
| WO | 2003/015678 A1 | | 2/2003 |
| WO | 2003/092677 A1 | | 11/2003 |
| WO | 2004/012721 A2 | | 2/2004 |
| WO | WO 2004/012730 | | 2/2004 |
| WO | 2004/050083 A1 | | 6/2004 |
| WO | 2005/009424 A1 | | 2/2005 |
| WO | 2005/063236 A1 | | 7/2005 |
| WO | 2005/063237 A1 | | 7/2005 |
| WO | 2005/092331 A1 | | 10/2005 |
| WO | 2005/119610 A1 | | 12/2005 |
| WO | 2008/061639 A1 | | 5/2008 |
| WO | 2009/068520 A2 | | 6/2009 |
| WO | WO 2010/042152 | | 4/2010 |
| WO | 2011/057714 A3 | | 5/2011 |
| WO | WO 2011/076879 | | 6/2011 |
| WO | 2012/071175 A1 | | 5/2012 |
| WO | WO 2012/084969 | | 6/2012 |
| WO | 2013/075823 A1 | | 5/2013 |
| WO | WO 2013/075822 | | 5/2013 |
| WO | 2013/088254 A1 | | 6/2013 |
| WO | WO 2014/079573 | | 5/2014 |
| WO | 2014/195352 A1 | | 12/2014 |

OTHER PUBLICATIONS

Dow Corning: Amine-Compatible Silicone Adhesives, Jul. 28, 2008.

Henkel Corporation, "DURO-TAK and GELVA Transdermal Pressure Sensitive Adhesives," Product Selection Guide, Sep. 2013.

H.F. Hammond in D. Satas "Handbook of Pressure Sensitive Adhesive Techology" (1989) 2nd ed., Chapter 4, Van Nostrand Reinhold, New York, p. 38.

Kandavilli, Sateesh et al., "Polymers in Transdermal Drug Delivery Systems," Pharmaceutical Technology, May 2002, pp. 62-80.

Fachinformation Neupro (Aug. 2011) with English Translation.

www.ucb.com/investors/Our-equity-story/Neupro(Jan. 6, 2016).

"Pressure Sensitive Tack of Adhesives Using an Inverted Probe Machine" ASTM D2979-71 (1982).

K.L. Ulman and R.P. Sweet, "The Correlation of Tape Properties and Rheology" (1998), Information Brochure, Dow Corning Corp., USA.

Chinese Search Report for the CN Application 201380054953.X, which corresponds to U.S. Appl. No. 14/443,210, filed May 15, 2015.

Dow Corning 360 Medical Fluid, (retrieved from on-line website; https://www.b2bcomposites.com/msds/ted/71115.pdf, pp. 1-7, 2010).

U.S. Appl. No. 15/312,433 PCT IntlSrchRpt International Search Report, PCT/EP2015/061112, which corresponds to U.S. Appl. No. 15/312,433, filed Nov. 18, 2016.

Chien, "Developmental Concepts and Practice in Transdermal Therapeutic Systems," Chapter 2 in Transdermal Controlled Systemic Medications, 1987, vol. 31, pp. 25-44.

JP Application No. 2018-147720 First Office Action, which corresponds to U.S. Appl. No. 16/009,613.

JP Application No. 2016-522618 First Office Action, which corresponds to U.S. Appl. No. 16/009,613.

JP Application No. 2016-522618 Second Office Action, which corresponds to U.S. Appl. No. 16/009,613.

Office Actions in U.S. Appl. No. 16/009,613, dated Nov. 7, 2019 and May 22, 2020.

Office Actions in U.S. Appl. No. 14/443,210, dated Nov. 21, 2019 and Jul. 21, 2020.

Office Actions in U.S. Appl. No. 15/312,433, dated Mar. 23, 2020 and Oct. 21, 2020.

Office Actions in U.S. Appl. No. 15/513,542, dated Nov. 20, 2019 and Jun. 26, 2020.

* cited by examiner

TRANSDERMAL DELIVERY SYSTEM CONTAINING ROTIGOTINE

The present application claims priority from International Patent Application No. PCT/EP2015/061099 filed on May 20, 2015, which claims priority from European Patent Application No. 14169009.9 filed on May 20, 2014, the disclosures of which are incorporated herein by reference in their entirety.

TECHNICAL FIELD OF THE INVENTION

The present invention relates to a transdermal therapeutic system (TTS) for the transdermal administration of rotigotine, and processes of manufacture, and uses thereof.

BACKGROUND OF THE INVENTION

The active ingredient rotigotine [(−)-5,6,7,8-tetrahydro-6-[propyl-[2-(2-thienyl)ethyl]-amino]-1-naphthalenol] is a non-ergolinic dopamine D1/D2/D3-receptor agonist that resembles dopamine structurally and has a similar receptor profile but a higher receptor affinity. Rotigotine is disclosed as active agent for treating patients suffering from Parkinson's disease, Parkinson's plus syndrome, depression and the restless-legs syndrome as well as for the treatment or prevention of dopaminergic neuron loss.

The only currently available pharmaceutical product containing rotigotine is a transdermal therapeutic system (TTS). Neupro® is formulated as a once-daily TTS which provides a constant delivery of rotigotine to the skin over the course of 24 hours in an amount sufficient to treat patients for a time period of 24 hours. Thus, the TTS needs to be replaced after 1 day. For convenience reasons it is desirable to provide a multi-day TTS for a longer exchange mode, e.g., a twice-weekly (3-, or 4-day dosing regimen), or a once-weekly exchange mode (7-day dosing regimen) instead of the once-daily exchange mode as currently provided by Neupro®.

The maintenance of sufficient permeation rates with minimum fluctuation during a multi-day administration, e.g. an administration over at least 3 days, 4 days or 7 days, is in particular challenging since an increase of the active agent loading seems limited, in particular in solvent-based systems. Furthermore, an increase of active agent concentration in the TTS matrix is limited by skin irritation caused by high concentrations of rotigotine.

Although hot-meltable systems as described in WO 2004/012721 accept a higher loading of rotigotine and allow for a release of rotigotine for up to 7 days in an in vitro skin permeation model, a higher fluctuation of the permeation rate of rotigotine over the administration period, as well as a decrease of the rotigotine permeation after several days occur. The teaching is also limited to hot-melt systems, which is a significant limitation since solvent-based systems provide a technically important alternative which allows milder processing conditions for the active agent and allows a more precise coating of the active agent-containing layer.

There continues to exsist a need in the art for transdermal therapeutic systems for the transdermal administration of rotigotine providing a continuous administration of therapeutically effective amounts of rotigotine base in particular over a period of several days (e.g. over at least 3 days, or 4 days, in particular over 7 days) with a constant delivery of rotigotine over the desired administration period.

OBJECTS AND SUMMARY OF THE INVENTION

It is an object of the present invention to provide a transdermal therapeutic system for the transdermal administration of rotigotine providing a continuous administration of therapeutically effective amounts of rotigotine base for 1 to 7 days during an administration period to the skin of the patient of 1 to 7 days (e.g. 7 days).

It is also an object of the present invention to provide a transdermal therapeutic system for the transdermal administration of rotigotine providing a reduced fluctuation of the therapeutically effective permeation rate of rotigotine base during an administration period to the skin of the patient of 1 to 7 days (e.g. 7 days).

It is a further object of the present invention to provide a transdermal therapeutic system for the transdermal administration of rotigotine which is skin-tolerant.

It is a further object of the present invention to provide a transdermal therapeutic system for the transdermal administration of rotigotine which complies with the needs of a convenient application in view of size and thickness and can easily and cost-effectively be prepared.

It is an object of certain embodiments of the present invention to provide a transdermal therapeutic system for the transdermal administration of rotigotine wherein therapeutically effective amounts of rotigotine base are provided for 3 days by said transdermal therapeutic system during an administration period to the skin of the patient of 3 days.

It is an object of certain embodiments of the present invention to provide a transdermal therapeutic system for the transdermal administration of rotigotine wherein therapeutically effective amounts of rotigotine base are provided for 4 days by said transdermal therapeutic system during an administration period to the skin of the patient of 4 days.

It is an object of certain embodiments of the present invention to provide a transdermal therapeutic system for the transdermal administration of rotigotine wherein therapeutically effective amounts of rotigotine base are provided for 7 days by said transdermal therapeutic system during an administration period to the skin of the patient of 7 days.

These objects and others are accomplished by the present invention, which according to one aspect relates to a transdermal therapeutic system for the transdermal administration of rotigotine, containing an therapeutically effective amount of rotigotine base in a self-adhesive layer structure, comprising
  A) a backing layer, and
  B) a rotigotine-containing biphasic layer, the biphasic layer having
    a) an outer phase having a composition comprising 75% to 100% of a polymer or a polymer mixture, and
    b) an inner phase having a composition comprising rotigotine base,
  wherein the inner phase forms dispersed deposits in the outer phase, and
  wherein the inner phase comprises
    i. rotigotine base, and
    ii. a polymer mixture comprising at least two hydrophilic polymers selected from at least two of the polymer groups:
      polyvinylpyrrolidones having a K-Value of at least 80, or from 80 to 200,
      polyvinylpyrrolidones having a K-Value of less than 80, or from 10 to 79,
      copolymers of vinyl caprolactam, vinylacetate and ethylene glycol, copolymers of vinylpyrrolidone and vinylacetate,
copolymers of ethylene and vinylacetate,
polyethylene glycols,
polypropylene glycols,
acrylic polymers,
modified celluloses,
wherein the polymer mixture in the inner phase is present in an amount sufficient so that said rotigotine base forms a solid solution with the polymer mixture in the inner phase, and C) optionally an additional skin contact layer.

According to one specific aspect the invention relates to a transdermal therapeutic system for the transdermal administration of rotigotine containing an therapeutically effective amount of rotigotine base in a self-adhesive layer structure, comprising A) a backing layer, and
B) a rotigotine-containing dried biphasic layer, the dried biphasic layer having
   a) an outer phase having a pressure-sensitive adhesive composition comprising 75% to 100% of pressure sensitive adhesive polysiloxanes, and
   b) an inner phase having a composition comprising rotigotine base,
   wherein the inner phase forms dispersed deposits in the outer phase, and
   wherein the inner phase comprises
      i. 16% to 26% of rotigotine base of said dried biphasic layer, and
      ii. a polymer mixture comprising polyvinylpyrrolidone having a K-Value of at least 80, or from 80 to 200, and polyvinylpyrrolidone having a K-Value of less than 80, or from 10 to 79,
      wherein the polymer mixture in the inner phase is present in an amount sufficient so that said rotigotine base forms a solid solution with the polymer mixture in the inner phase,
   wherein the dried biphasic layer has an area weight of about 100 $g/m^2$ to about 200 $g/m^2$, and C) optionally an additional skin contact layer.

According to one specific aspect the invention relates to a transdermal administration of rotigotine containing 2.0 $mg/cm^2$ to 4.0 $mg/cm^2$ of rotigotine base in a self-adhesive layer structure, comprising A) a backing layer, and
B) a rotigotine-containing biphasic layer, the biphasic layer having
   a) an outer phase having a pressure-sensitive adhesive composition comprising 75% to 100% of pressure sensitive adhesive polysiloxanes, and
   b) an inner phase having a composition comprising rotigotine base,
   wherein the inner phase forms dispersed deposits in the outer phase, and
   wherein the inner phase comprises
      i. rotigotine base, and
      ii. a polymer mixture comprising polyvinylpyrrolidone having a K-Value of at least 80, or from 80 to 200, and polyvinylpyrrolidone having a K-Value of less than 80, or from 10 to 79,
      wherein the polymer mixture in the inner phase is present in an amount sufficient so that said rotigotine base forms a solid solution with the polymer mixture in the inner phase,
      wherein the ratio of rotigotine base to polyvinylpyrrolidone having a K-Value of less than 80, or from 10 to 79 is 1:0.1 to 1:0.5,
   wherein the biphasic layer has an area weight of about 100 $g/m^2$ to about 200 $g/m^2$, and C) an additional skin contact layer.

According to one specific aspect the invention relates to a transdermal therapeutic system for the transdermal administration of rotigotine containing an therapeutically effective amount of rotigotine base in a self-adhesive layer structure, comprising A) a backing layer, and
B) a rotigotine-containing biphasic layer, the biphasic layer having
   a) an outer phase having a pressure-sensitive adhesive composition comprising 75% to 100% of pressure-sensitive adhesive polysiloxanes, and
   b) an inner phase having a composition comprising rotigotine base,
   wherein the inner phase forms dispersed deposits in the outer phase, and
   wherein the inner phase comprises
      i. 10% to 30% of rotigotine base of said biphasic layer, and
      ii. a polymer mixture comprising polyvinylpyrrolidone having a K-Value of at least 80, or from 80 to 200, and polyvinylpyrrolidone having a K-Value of less than 80, or from 10 to 79,
      wherein the polymer mixture in the inner phase is present in an amount sufficient so that said amount of rotigotine base forms a solid solution with the polymer mixture in the inner phase,
   wherein the biphasic layer has an area weight of about 100 $g/m^2$ to about 200 $g/m^2$, and C) an additional rotigotine-containing skin contact layer which is also in the form of a biphasic layer having
   a) an outer phase having a pressure-sensitive adhesive composition comprising 75% to 100% of pressure-sensitive adhesive polysiloxanes, and
   b) an inner phase having a composition comprising rotigotine base,
   wherein the inner phase forms dispersed deposits in the outer phase, and
   wherein the inner phase comprises
      i. from 1% to 8% rotigotine base of said skin contact layer, and
      ii. polyvinylpyrrolidone having a K-Value of at least 80, or from 80 to 200, wherein said polyvinylpyrrolidone is present in an amount sufficient so that said amount of rotigotine base forms a solid solution with said polyvinylpyrrolidone,
   wherein the skin contact layer has an area weight of about 10 $g/m^2$ to about 150 $g/m^2$.

According to certain embodiments of the invention, the transdermal therapeutic system according to the invention is for use in a method of treatment, in particular for use in a method of treating patients suffering from Parkinson's disease, Parkinson's plus syndrome, depression, anxiety, AHDS, fibromyalgia, the restless-legs syndrome and for use in the treatment or prevention of dopaminergic neuron loss or the treatment or prevention of cognitive disorders, dementia or lewy body disease, in particular by applying a transdermal therapeutic system for about 168 hours (corresponding to 7 days or one week) on the skin of a patient.

The transdermal therapeutic system according to the invention provides therapeutically effective amounts of rotigotine base for 1 to 7 days by the transdermal therapeutic system according to the invention during an administration period to the skin of the patient of 1 to 7 days, preferably for 3 days during an administration period to the skin of the patient of 3 days, more preferably for 4 days during an administration period to the skin of the patient of 4 days, most preferred for 7 days during an administration period to the skin of the patient of 7 days.

According to one aspect, the invention relates to the use of a polymer mixture of polyvinylpyrrolidone having a K-Value of at least 80, or from 80 to 200, and polyvinylpyrrolidone having a K-Value of less than 80, or from 10 to 79, in the manufacture of a transdermal therapeutic system for the transdermal administration of rotigotine to provide dispersed solid solution deposits of the polymer mixture including rotigotine base in a pressure-sensitive adhesive composition comprising pressure-sensitive adhesive polysiloxane(s) to control the release of rotigotine base.

According to one specific aspect the invention relates to a method of manufacture of a transdermal therapeutic system for the transdermal administration of rotigotine in accordance with the invention, comprising the steps of:
(1) preparing a rotigotine-containing biphasic coating mixture having an inner phase dispersed in an outer phase,
(2) coating said rotigotine-containing biphasic coating mixture on a film in an amount to provide a coated layer,
(3) drying said coated layer to provide a dried layer with a coating weight to provide a rotigotine-containing dried biphasic layer with the desired area weight,
(4) optionally laminating two or more of said dried layers to provide a rotigotine-containing dried biphasic layer with the desired area weight,
(5) laminating said rotigotine-containing dried biphasic layer to a backing layer,
(6) optionally laminating said rotigotine-containing dried biphasic layer to an additional skin contact layer,
preferably wherein for the production of the biphasic layer and optionally the additional skin contact layer a pressure-sensitive adhesive mixture of pressure-sensitive adhesive polysiloxanes in heptane or ethyl acetate is used.

According to certain embodiments of the invention, the preparation of the rotigotine-containing biphasic coating mixture comprises the steps of:
(1) mixing a polymer mixture comprising at least two hydrophilic polymers selected from at least two of the polymer groups:
  polyvinylpyrrolidones having a K-Value of at least 80, or from 80 to 200,
  polyvinylpyrrolidones having a K-Value of less than 80, or from 10 to 79,
  copolymers of vinyl caprolactam, vinylacetate and ethylene glycol,
  copolymers of vinylpyrrolidone and vinylacetate,
  copolymers of ethylene and vinylacetate,
  polyethylene glycols,
  polypropylene glycols,
  acrylic polymers,
  modified celluloses,
  with a solvent to obtain a solution,
(2) optionally adding tocopherol, ascorbyl palmitate, and an aqueous sodium metabisulfite solution to the solution of step 1,
(3) adding rotigotine base and a mixture of a composition comprising 75% to 100% of a polymer or a polymer mixture in a solvent to said solution to provide a rotigotine-containing biphasic coating mixture.

According to certain embodiments of the invention, the rotigotine-containing biphasic layer is laminated to an additional skin contact layer and the skin contact layer is prepared comprising the steps of:
(1) providing an adhesive coating mixture, preferably a rotigotine-containing biphasic coating mixture having an inner phase dispersed in an outer phase and comprising at least one hydrophilic polymer in the inner phase,
(2) coating said adhesive coating mixture on a film to provide a layer of said adhesive coating mixture,
(3) drying said coated layer to provide a dried layer with a coating weight to provide said skin contact layer with the desired area weight,
(4) optionally laminating two or more of said dried layers to provide said skin contact layer with the desired area weight.

Within the meaning of this invention, the term "transdermal therapeutic system" (or TTS) refers to a system by which the active agent (rotigotine) is administered systemically and in particular refers to the entire individual unit that is applied to the skin of a patient, and which comprises an therapeutically effective amount of rotigotine base in a self-adhesive layer structure and optionally an additional larger active-free self-adhesive layer structure (overlaying adhesive) on top of the rotigotine-containing self-adhesive layer structure. During storage, such a TTS is normally located on a detachable protective layer from which it is removed immediately before application to the surface of the patient's skin. A TTS protected this way may be stored in a blister pack or a side sealed bag.

Within the meaning of this invention, the term "active", "active agent", and the like, as well as the term "rotigotine" refer to rotigotine base. The term rotigotine base, however, means that rotigotine base is used in the manufacture of the TTS but does not exclude interactions between the rotigotine base and other ingredients of the rotigotine-containing biphasic layer, e.g. polyvinylpyrrolidone. Unless otherwise indicated, the amounts of rotigotine in the self-adhesive layer structure relate to the amount of rotigotine base included in the TTS during manufacture of the TTS.

Within the meaning of this invention, the term "rotigotine-containing self-adhesive layer structure" refers to the active agent-containing structure providing the area of rotigotine release during administration. The overlaying adhesive adds to the overall size of the TTS but does not add to the area of release. The rotigotine-containing self-adhesive layer structure comprises a backing layer, a rotigotine-containing biphasic layer and optionally an additional skin contact layer.

Within the meaning of this invention, the term "biphasic" refers to a system of two distinguishable, e.g., visually distinguishable, areas, an outer phase and an inner phase, wherein the inner phase is in form of dispersed deposits within the outer phase. Such deposits are e.g., solid solution droplets. Deposits that are visually distinguishable may be identified by use of a microscope.

Within the meaning of this invention, the term "biphasic layer" refers to the final biphasic layer solidified after coating the coating mixture by e.g. drying a solvent-containing coating mixture or cooling a hot-melt coating mixture. Solvent-containing coating mixtures are preferred according to the invention. The biphasic layer may also be manufactured by laminating two or more layers (e.g. dried layers) of the same composition to provide the desired area weight.

Within the meaning of this invention, the term "dried biphasic layer" refers to a biphasic layer obtained from a solvent-containing coating mixture after coating on a film and evaporating the solvents (solvent-based layer) and is to be distinguished from a biphasic layer obtained from a hot-melt coating mixture (hot-melt-based layer).

If not indicated otherwise "%" refers to weight-%.

Within the meaning of this invention, the term "polymer mixture" includes mixtures of polymers comprising the same monomer(s) but providing different grades. Polymers of different grades are polymers which are distinguishable by different properties (e.g. the viscosity) and are usually commercially available under different trademarks. E.g., the commercially available products Kollidon® 90 and Kollidon® 30 provide individual grades of polyvinylpyrrolidone, a polymer of the monomer vinylpyrrolidon; the commercially available products Dow Corning® BIO-PSA 7-4201 and BIO-PSA 7-4301 provide individual grades of pressure-sensitive adhesive polysiloxane.

Within the meaning of this invention, the term "solid solution" refers to a mixture of active agent (rotigotine base) and the polymer mixture to provide a single homogeneous phase in form of a solid-state solution.

Within the meaning of this invention, the term "pressure-sensitive adhesive composition" refers to a composition that in particular adheres with finger pressure, is permanently tacky, exerts a strong holding force and should be removable from smooth surfaces without leaving a residue. The pressure-sensitive adhesive properties of the pressure-sensitive adhesive composition are based on suitable tackifiers, or on a polymer or polymer mixture which is a/are pressure-sensitive adhesive polymer(s), or on both. Pressure-sensitive adhesive polymers are available in solid form or in a mixture with a suitable solvent (e.g. heptanes or ethyl acetat). According to a certain embodiment, the polymer or polymer mixture is a/are pressure-sensitive adhesive polysiloxane(s). Examples of useful pressure-sensitive adhesive polysiloxanes which are commercially available include the standard BIO-PSA series (7-4400, 7-4500 and 7-4600 series), the amine compatible (endeapped) BIO-PSA series (7-4100, 7-4200 and 7-4300 series), the Soft Skin Adhesives series (7-9800), and the BIO-PSA Hot Melt Adhesives manufactured by Dow Corning. Preferred pressure-sensitive polysiloxanes are heptane- and ethyl acetate-solvated pressure-sensitive adhesive polysiloxanes including BIO-PSA 7-4201, BIO-PSA 7-4301, BIO-PSA 7-4202, and BIO-PSA 7-4302.

Within the meaning of this invention, the term "pressure-sensitive adhesive mixture" refers to a pressure-sensitive adhesive polymer or pressure-sensitive adhesive polymers at least in mixture with a solvent (e.g., heptanes or ethyl acetat).

Within the meaning of this invention, the term "polyvinylpyrrolidone" refers to polyvinylpyrrolidone which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon® 12 PF, Kollidon® 17 PF, Kollidon® 25, Kollidon® 30 and Kollidon® 90 F supplied by BASF. The different grades of Kollidon® are defined in terms of the K-Value reflecting the average molecular weight of the polyvinylpyrrolidone grades. Kollidon® 12 PF is characterized by a K-Value range of 10.2 to 13.8, corresponding to a nominal K-Value of 12. Kollidon® 17 PF is characterized by a K-Value range of 15.3 to 18.4, corresponding to a nominal K-Value of 17. Kollidon® 25 is characterized by a K-Value range of 22.5 to 27.0, corresponding to a nominal K-Value of 25, Kollidon® 30 is characterized by a K-Value range of 27.0 to 32.4, corresponding to a nominal K-Value of 30. Kollidon® 90 F is characterized by a K-Value range of 81.0 to 97.2, corresponding to a nominal K-Value of 90. Preferred Kollidon® grades are Kollidon® 30 and Kollidon® 90 F.

Within the meaning of this invention, the term "K-Value" refers to a value calculated from the relative viscosity of polyvinylpyrrolidone in water according to the European Pharmacopoeia (Ph.Eur.) and USP monographs for "Povidone".

Within the meaning of this invention, the term "skin contact layer" refers to the part of the TTS which is an additional layer (in addition to the rotigotine-containing biphasic layer) and is in direct contact with the skin of the patient during administration. The sizes of an additional skin contact layer and the rotigotine-containing self-adhesive layer structure are co-extensive and correspond to the area of release.

Within the meaning of this invention, the term "additional larger active agent-free self-adhesive layer structure" (overlaying adhesive) refers to a self-adhesive layer structure that is free of active agent and larger in area than the active agent-containing structure and providing additional area adhering to the skin, but no area of release of the active agent, and enhancing thereby the overall adhesive properties of the TTS.

Within the meaning of this invention, the term "area weight" refers to the dry weight of an individual layer or the sum of individual layers, except backing layer and release liner, and is provided in $g/m^2$. The area weight may be the coating weight of a layer, or the sum of the coating weights of individual layers. Amounts of active agent or polymer in a layer provided in $mg/cm^2$ or % refer to or are based on the area weight of the layer.

Within the meaning of this invention, the parameter "rotigotine permeation" is provided in $\mu g/cm^2$ and relates to the amount rotigotine permeated at a certain elapsed time within the total time period of permeation as measured in an in vitro rotigotine permeation test performed over an extended period of time using a 51 µm thick membrane consisting of an ethylene vinyl acetate (EVA) copolymer with 9% vinyl acetate (CoTran™ Membrane, 3M) and the Paddle over Disk apparatus described in the United States Phamacopeia (USP). Phosphate buffer pH 4.5 was used as acceptor medium (900 ml; 32° C.; 50 rpm). The rotigotine permeation rate into the acceptor medium was determined in regular intervals using a validated UV photometric or HPLC method, determination by HPLC is preferred. The time between sampling and determination of permeated rotigotine in the sample should not exceed 24 hours and is preferably less than 1 hour. The value is a mean value of at least 3 experiments.

Within the meaning of this invention, the parameter "rotigotine permeation rate" is provided in $\mu g/cm^2/hr$ and is calculated from the permeation of rotigotine of a certain sample interval, e.g. from hour 8 to hour 12, as measured through an EVA membrane in $\mu g/cm^2$ divided by the hours of said sample interval, e.g. 4 hours.

Within the meaning of this invention, the parameter "rotigotine skin permeation" is provided in $\mu g/cm^2$ and relates to the amount rotigotine permeated at a certain elapsed time within the total time period of permeation as measured in an in vitro rotigotine skin permeation test performed over an extended period of time using dermatomized human skin of about 300 μm thickness in a flow cell setup. A phosphate buffered saline (PBS) pH 6.2 was used as acceptor medium (32° C.). The rotigotine skin permeation rate into the acceptor medium was determined in regular intervals using a validated UV photometric or HPLC method, determination by HPLC is preferred. The time between sampling and determination of permeated rotigotine in the sample should not exceed 24 hours and is preferably less than 1 hour. The value is a mean value of at least 3 experiments.

Within the meaning of this invention, the parameter "rotigotine skin permeation rate" is provided in $\mu g/cm^2/hr$ and is calculated from the permeation of rotigotine of a certain sample interval, e.g. from hour 9 to hour 12, as measured in vitro through human skin in $\mu g/cm^2$ divided by the hours of said sample interval, e.g. 3 hours.

DETAILED DESCRIPTION

TTS Structure

Figure 1:
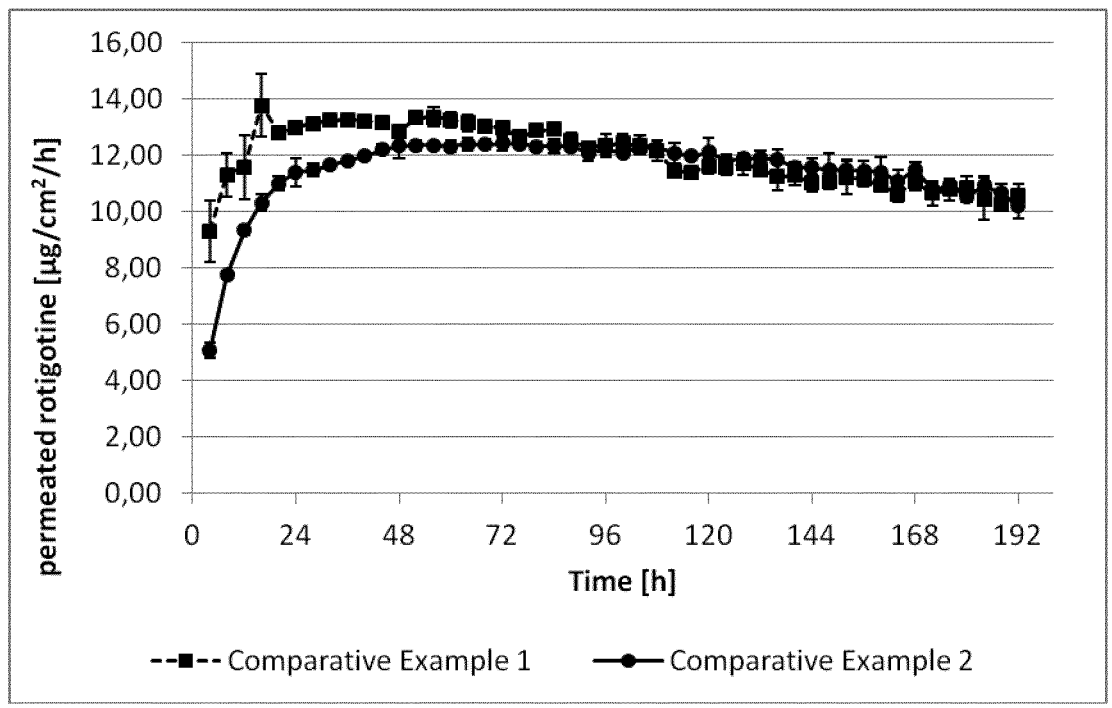
FIG. 1 depicts the rotigotine permeation rate of Comparative Example 1 and Comparative Example 2.
Figure 2:
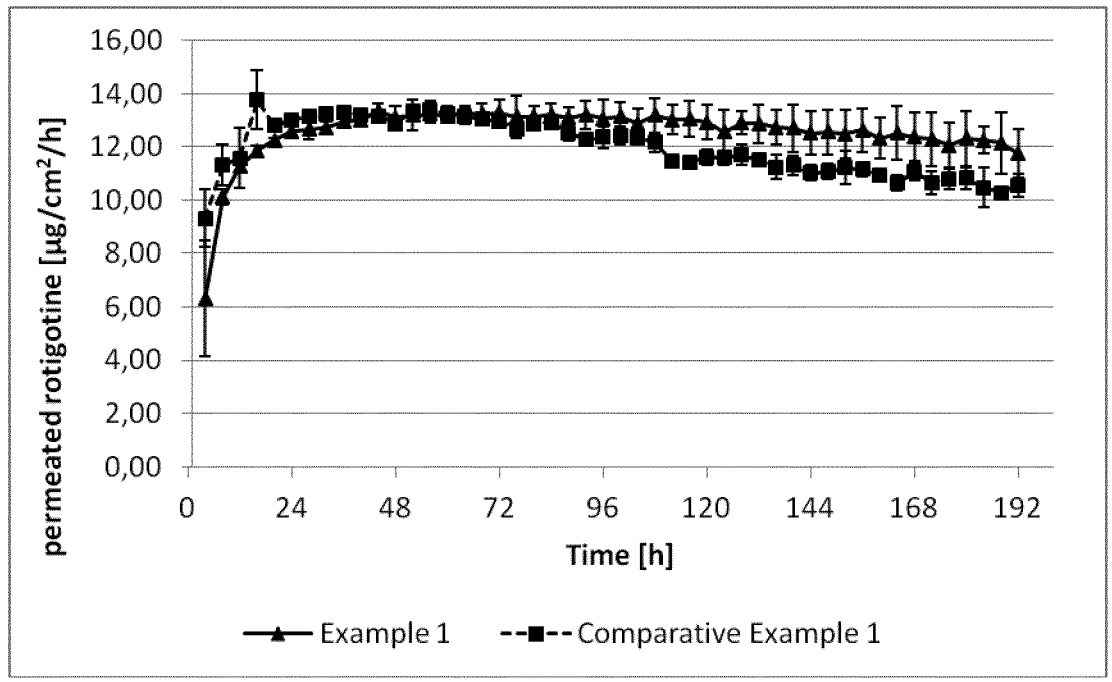
FIG. 2 depicts the rotigotine permeation rate of Example 1 and Comparative Example 1.
Figure 3:
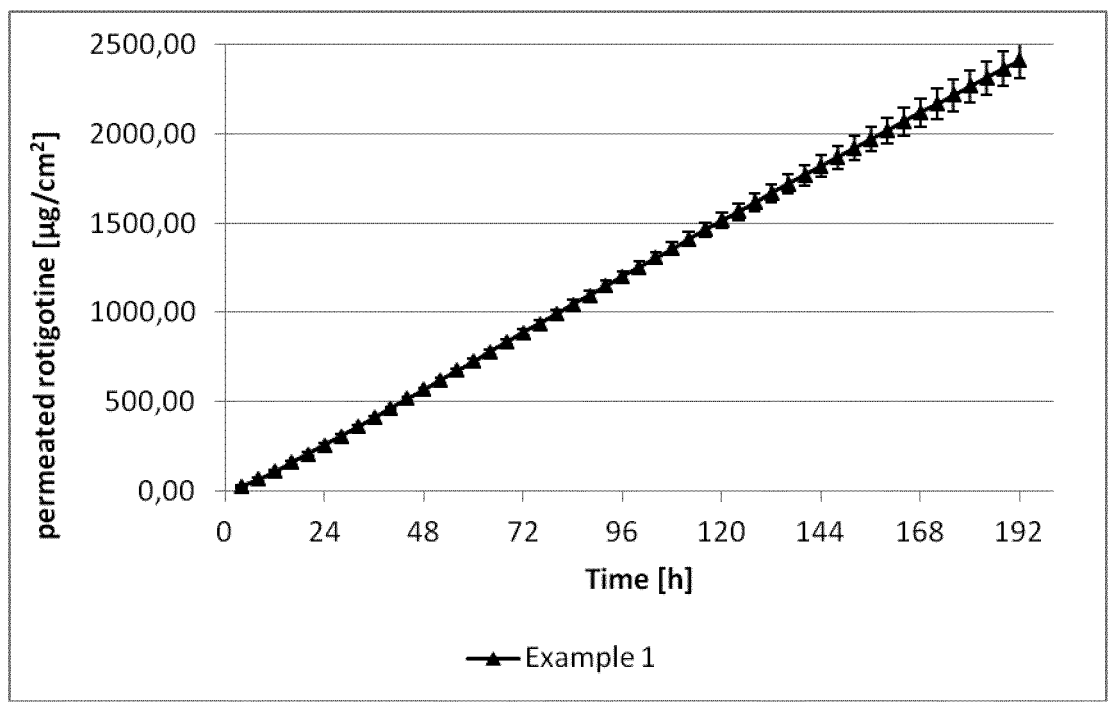
FIG. 3 depicts the rotigotine permeation of Example 1.
Figure 4:
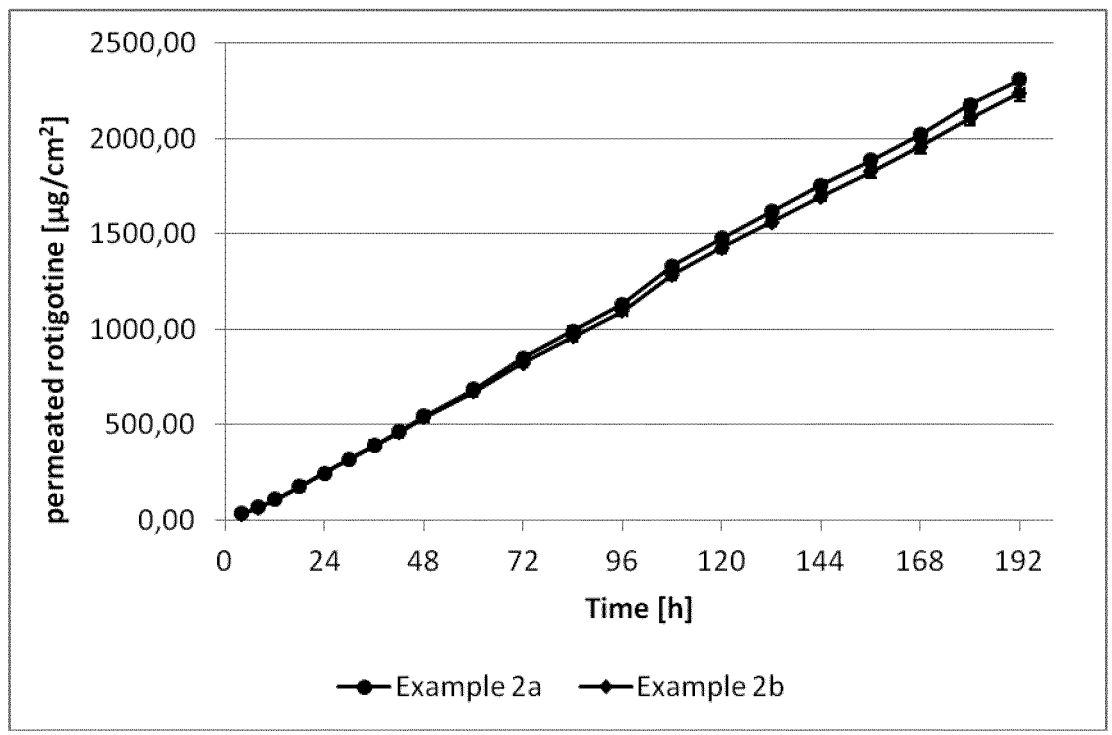
FIG. 4 depicts the rotigotine permeation of Examples 2a and 2b.

According to a certain embodiment of the invention the transdermal therapeutic system for the transdermal administration of rotigotine comprises an therapeutically effective amount of rotigotine base in a self-adhesive layer structure, comprising
  A) a backing layer, and
  B) a rotigotine-containing biphasic layer, the biphasic layer having
    a) an outer phase having a composition comprising 75% to 100% of a polymer or a polymer mixture, and
    b) an inner phase having a composition comprising rotigotine base,
    wherein the inner phase forms dispersed deposits in the outer phase, and
    wherein the inner phase comprises
      i. rotigotine base, and
      ii. a polymer mixture comprising at least two hydrophilic polymers selected from at least two of the polymer groups:
        polyvinylpyrrolidones having a K-Value of at least 80, or from 80 to 200,
        polyvinylpyrrolidones having a K-Value of less than 80, or from 10 to 79,
        copolymers of vinyl caprolactam, vinylacetate and ethylene glycol,
        copolymers of vinylpyrrolidone and vinylacetate,
        copolymers of ethylene and vinylacetate,
        polyethylene glycols,
        polypropylene glycols,
        acrylic polymers,
        modified celluloses,
      wherein the polymer mixture in the inner phase is present in an amount sufficient so that said rotigotine base forms a solid solution with the polymer mixture in the inner phase,
    and
  C) optionally an additional skin contact layer.

Without wishing to be bound to any theory it is believed that the polymer mixture in the inner phase comprising at least two hydrophilic polymers from at least two of the polymer groups described in the previous paragraph controls the permeation rate of rotigotine during an administration period to the skin of the patient of 1 to 7 days, in particular of 7 days.

According to certain embodiments of the invention, the TTS may comprise in addition to the rotigotine-containing self-adhesive layer structure attached thereto a larger active agent-free self-adhesive layer structure, e.g., an overlaying adhesive, for enhancing the adhesive properties of the overall transdermal therapeutic system. Said active agent-free self-adhesive layer structure comprises also a backing layer. In certain embodiments, this additional layer is beige colored. The area of said second active agent-free self-adhesive layer structure adds to the overall size of the TTS but does not add to the area of release. The pressure-sensitive adhesive compositions of the active agent-containing and the active agent-free self-adhesive layer structures may be the same or different. E.g., the active agent-free pressure-sensitive adhesive composition may comprise a pressure-sensitive adhesive polymer or polymer mixture selected from the group of polyacrylates or polysiloxanes.

A TTS according to the invention is normally located on a detachable protective layer (release liner) from which it is removed immediately before application to the surface of the patient's skin. A TTS protected this way may be stored in a blister pack or a side sealed bag.

Rotigotine-Containing Self-Adhesive Layer Structure

In accordance with the invention, the rotigotine-containing self-adhesive layer structure comprises a backing layer, a rotigotine-containing biphasic layer and optionally an additional skin contact layer.

The rotigotine-containing self-adhesive layer structure may contain an therapeutically effective amount of rotigotine base from 0.1 $mg/cm^2$ to 10.0 $mg/cm^2$, in particular from 0.1 $mg/cm^2$ to 5.0 $mg/cm^2$, or from 0.3 $mg/cm^2$ to 3.0 $mg/cm^2$. According to certain embodiments, the TTS contains from 0.3 $mg/cm^2$ to 1.0 $mg/cm^2$ (for 1 day), or from 1.0 $mg/cm^2$ to 1.5 $mg/cm^2$ (for 3 days, or 4 days), or from 1.5 $mg/cm^2$ to 5.0 $mg/cm^2$ (for 7 days), or from 2.0 $mg/cm^2$ to 4.0 $mg/cm^2$ (for 7 days), or from 2.0 $mg/cm^2$ to 3.0 $mg/cm^2$ (for 7 days) rotigotine base in the self-adhesive layer structure.

It was found that the amount of rotigotine base being required for the continuous administration of therapeutically effective amounts of rotigotine base preferably for at least 3 days and up to at least 7 days by the transdermal therapeutic system of the invention was lower than expected and calculated for the respective number of single-day transdermal therapeutic systems known from the prior art. E.g., the commercial product Neupro® contains 0.45 $mg/cm^2$ for an application period of 24 hours to provide therapeutically effective amounts of rotigotine base for 1 day, i.e., the single-day transdermal therapeutic system known from the prior art contains 0.45 $mg/cm^2$/day. According to a certain embodiment, the TTS of the invention contains from about 0.3 mg/cm$^2$/day to about 0.4 mg/cm$^2$/day rotigotine base in the self-adhesive layer structure and is suitable for a continuous administration of therapeutically effective amounts of rotigotine base for 7 days during an administration period to the skin of the patient of 7 days.

The size of the rotigotine-containing self-adhesive layer structure providing the area of release ranges from 1 cm$^2$ to 60 cm$^2$, and may be about 5 cm$^2$, about 10 cm$^2$, about 20 cm$^2$, about 30 cm$^2$, about 40 cm$^2$, or about 50 cm$^2$. The amount of rotigotine provided by the TTS per hour (mg/h) is proportional to the size of the area of release of a TTS and may be used to distinguish TTS by the dosage strength.

If the self-adhesive layer structure according to the invention comprises an additional rotigotine-containing skin contact layer, rotigotine base is present in the skin contact layer in a smaller amount than in said biphasic layer based on the area weight of each layer.

Rotigotine exists in two different polymorphic states, Polymorphic Form I and Polymorphic Form II, which can be differentiated by their melting point, infrared (IR) spectroscopy, solid state nuclear magnetic resonance (SSNMR) or Raman spectroscopy as well as differential scanning calorimetry (DSC) and X-ray powder diffraction (XRD). The different physicochemical characteristics of the two polymorphic forms of rotigotine are for example described in WO 2009/068520. For the TTS according to the invention, Polymorphic Form II is preferred.

Biphasic Layer

The biphasic layer contains an outer and an inner phase.

The rotigotine-containing biphasic layer may be coated at any area weight, but is preferably coated at an area weight of about 30 g/m$^2$ to about 400 g/m$^2$, or of about 30 g/m$^2$ to about 200 g/m$^2$, or of about 100 g/m$^2$ to about 200 g/m$^2$.

The rotigotine-containing biphasic layer contains rotigotine base in an amount of 1% to 30%, 10% to 26%, or 16% to 30%, or 16% to 26% of the biphasic layer.

According to a certain embodiment, the biphasic layer has an area weight of about 100 g/m$^2$ to about 200 g/m$^2$ and rotigotine base is present in an amount of 16% to 26% of the biphasic layer.

According to a certain embodiment, the biphasic layer is a dried biphasic layer. The dried biphasic layer is obtained from a solvent-containing biphasic coating mixture after coating on a film and evaporating the solvents. The obtained layer (solvent-based layer) is to be distinguished from a biphasic layer obtained from a hot-melt coating mixture (hot melt-based layer). A biphasic layer obtained from a hot-melt coating mixture is characterized by different physico-chemical properties.

According to a certain embodiment of the invention, the rotigotine-containing biphasic layer is in direct contact with the skin.

According to a certain other embodiment of the invention, the rotigotine-containing self-adhesive layer structure comprises an additional skin contact layer which is also in the form of a biphasic layer and may be manufactured containing rotigotine base, preferably in an amount of 1% to 15%, more preferably of less than 9%, or from 1% to 8% of the skin contact layer. The additional rotigotine-containing skin contact layer may be coated at any area weight, but is preferably coated at an area weight of about 10 g/m$^2$ to about 150 g/m$^2$.

The biphasic layer of the TTS according to the invention may further comprise one or more anti-oxidants. Suitable anti-oxidants are sodium metabisulfite, ascorbyl palmitate, tocopherol and esters thereof, ascorbic acid, butylhydroxytoluene, butylhydroxyanisole or propyl gallate, preferably sodium metabisulfite, ascorbyl palmitate and tocopherol. The anti-oxidants may be conveniently present in an amount of from about 0.001 to about 0.5% of the rotigotine-containing biphasic layer.

The biphasic layer according to the invention may further comprise in addition to the above mentioned ingredients other various excipients or additives, for example from the group of solubilizers, fillers, tackifiers, substances which influence the barrier properties of the stratum corneum in the sense of increasing the active agent permeability, pH regulators, and preservatives. Suitable permeation enhancers may be selected from the group of fatty alcohols, fatty acids, fatty acid esters, fatty acid amides, glycerol or its fatty acid esters, N-methylpyrrolidone, terpenes such as limonene, [alpha]-pinene, [alpha]-terpineol, carvone, carveol, limonene oxide, pinene oxide, 1,8-eucalyptol and most preferably ascorbyl palmitate. In a preferred embodiment, the TTS according to the invention does not contain a penetration enhancer.

Outer Phase

In accordance with the invention, the outer phase of the rotigotine-containing biphasic layer is a composition comprising 75% to 100% of a polymer or a polymer mixture. The polymer or polymer mixture in the outer phase may be a hydrophobic polymer or hydrophobic polymers.

In a certain embodiment of the invention, the composition of said outer phase is a pressure-sensitive adhesive composition.

In certain other embodiments of the invention, the polymer or polymer mixture in the outer phase is a/are pressure-sensitive adhesive polymer(s).

Pressure-sensitive adhesive polymers being suitable for a hot-melt coating exhibit a dynamic viscosity of no more than 60 Pa·s, no more than 80 Pa·s, no more than 100 Pa·s, no more than 120 Pa·s or at most 150 Pa·s at a temperature of 160° C. Depending on the dynamic viscosity of the pressure-sensitive adhesive polymer(s) at 160° C., the addition of a softener, such as waxes, silicone oils, glycerin, condensates from glycerin with fatty acids or polyols, or laurylacetate, or, in particular, glycerolmonolaurate, laurylacetate, waxes of the formula R—C(O)—OR', alkylmethylsiloxane waxes, siloxated polyether waxes, organic waxes or glycerin, may be required to adjust the viscosity of the pressure-sensitive adhesive polymer(s) in a suitable manner during hot-melt manufacturing processes.

Pressure-sensitive adhesive polymers being suitable for solvent-containing coating mixtures exhibit a dynamic viscosity of above 150 Pa·s at a temperature of 160° C. and therefore require the addition of a softener in order to be suitable for a hot-melt manufacturing process.

According to a certain embodiment of the invention, the pressure-sensitive adhesive composition does not contain a softener, which after the addition to an pressure-sensitive adhesive composition lowers the viscosity of said pressure-sensitive adhesive composition to no more than 60 Pa·s, no more than 80 Pa·s, no more than 100 Pa·s, no more than 120 Pa·s or at most 150 Pa·s at a temperature of 160° C.

According to a certain embodiment of the invention, the outer phase does not contain a pressure-sensitive adhesive composition having a dynamic viscosity of no more than 60

Pa·s, no more than 80 Pa·s, no more than 100 Pa·s, no more than 120 Pa·s or at most 150 Pa·s at a temperature of 160° C.

In certain embodiments of the invention, the polymer or polymer mixture in the outer phase is a/are pressure-sensitive adhesive polymer(s) selected from the group of polysiloxanes, polyisobutylenes, polyacrylates, copolymers of styrene and butadiene, copolymers of styrene and isoprene, preferably selected from the group of polysiloxanes, or polyisobutylenes.

In a certain preferred embodiment of the invention, the polymer or polymer mixture in the outer phase is a/are pressure-sensitive adhesive polysiloxane(s). Pressure-sensitive adhesive polysiloxanes provide for suitable tack for quick bonding to various skin types, including wet skin, suitable adhesive and cohesive qualities, long lasting adhesion to the skin of up to 7 days, a high degree of flexibility, a permeability to moisture, and compatibility to many actives and film-substrates. It is possible to provide them with sufficient amine resistance and therefore enhanced stability in the presence of amines. Such pressure-sensitive adhesive polymers are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The dimethiconol content contributes to the viscous component of the visco-elastic behavior, and impacts the wetting and the spreadability properties of the adhesive. The resin acts as a tackifying and reinforcing agent, and participates in the elastic component. The correct balance between dimethiconol and resin provides for the correct adhesive properties.

The adhesive strength of the pressure-sensitive polysiloxanes may be sufficient for the desired skin contact. In certain embodiments of the invention a plasticizer or a tackifying agent is incorporated into the formulation to improve the adhesive characteristics of the biphasic layer. It may be advantageous in an individual case to improve the tack by adding small amounts of tackifiers.

Preferred pressure-sensitive adhesive polymers are supplied and used in solvents like heptane, ethyl acetate or other volatile silicone fluids. For the present invention pressure-sensitive adhesive mixtures of pressure-sensitive adhesive polysiloxane(s) in heptane or ethyl acetate are preferred. The solids content is usually between 60 and 80%.

The preferred pressure-sensitive adhesive mixtures of pressure-sensitive adhesive polysiloxane(s) in heptane in accordance with the invention are characterized by a solution viscosity at 25° C. and 60% solids content in heptane of more than 150 mPa s, or from about 200 mPa s to about 700 mPa s, in particular from about 350 mPa s to about 600 mPa s, more preferred from about 480 mPa s to about 550 mPa s, or most preferred of about 500 mPa s or alternatively from about 400 mPa s to about 480 mPa s, or most preferred of about 450 mPa s. These may also be characterized by a complex viscosity at 0.01 rad/s at 30° C. of less than about $1\times10^9$ Poise or from about $1\times10^5$ to about $9\times10^8$ Poise, or more preferred from about $1\times10^5$ to about $1\times10^7$ Poise, or most preferred about $5\times10^6$ Poise or alternatively more preferred from about $2\times10^7$ to about $9\times10^8$ Poise, or most preferred about $1\times10^8$ Poise.

The preferred pressure-sensitive adhesive mixtures of pressure-sensitive adhesive polysiloxane(s) in ethyl acetate in accordance with the invention are characterized by a solution viscosity at 25° C. and 60% solids content in ethyl acetate of more than 350 mPa s, or from about 400 mPa s to about 1500 mPa s, in particular from about 600 mPa s to about 1300 mPa s, more preferred from about 1100 mPa s to about 1300 mPa s, or most preferred of about 1200 mPa s or alternatively from about 700 mPa s to about 900 mPa s, or most preferred of about 800 mPa s. These may also be characterized by a complex viscosity at 0.01 rad/s at 30° C. of less than about $1\times10^9$ Poise or from about $1\times10^5$ to about $9\times10^8$ Poise, or more preferred from about $1\times10^5$ to about $1\times10^7$ Poise, or most preferred about $5\times10^6$ Poise or alternatively more preferred from about $2\times10^7$ to about $9\times10^8$ Poise, or most preferred about $1\times10$ Poise.

According to a certain embodiment, a pressure-sensitive adhesive mixture of a pressure-sensitive adhesive polysiloxane in heptane characterized by a solution viscosity at 25° C. and about 60% solids content in heptane of 500 mPa s and a pressure-sensitive adhesive polysiloxane in heptane characterized by a solution viscosity at 25° C. and about 60% solids content in heptane of 450 mPa s is preferred.

According to a certain other embodiment, a pressure-sensitive adhesive mixture of a pressure-sensitive adhesive polysiloxane in ethyl acetate characterized by a solution viscosity at 25° C. and about 60% solids content in ethyl acetate of 1200 mPa s and a pressure-sensitive adhesive polysiloxane in ethyl acetate characterized by a solution viscosity at 25° C. and about 60% solids content in ethyl acetate of 800 mPa s is preferred.

Suitable pressure-sensitive adhesive polysiloxanes may be obtained from Dow Corning® BIO-PSA Standard Silicone Adhesives. Preferred pressure-sensitive adhesive mixtures of pressure-sensitive adhesive polysiloxane(s) in heptane are the BIO-PSA 7-4301 and BIO-PSA 7-4201 Silicone Adhesives, and in ethyl acetate the BIO-PSA 7-4302 and BIO-PSA 7-4202 Silicone Adhesives. According to certain embodiments of the invention, a mixture of BIO-PSA 7-4301 and BIO-PSA 7-4201 is preferred and according to certain other embodiments a mixture of BIO-PSA 7-4302 and BIO-PSA 7-4202 is preferred. According to certain embodiments the preferred mixtures provide a 50:50 ratio, according to certain other embodiments the mixtures provide a 60:40, or 70:30 ratio. A higher amount of BIO-PSA 7-4301, or BIO-PSA 7-4302, respectively, is preferred for a biphasic layer which provides the skin contact layer. According to a certain embodiment of the invention, the TTS comprises a mixture of BIO-PSA 7-4301 and BIO-PSA 7-4201 in a ratio of 30:70 in the outer phase of the rotigotine-containing biphasic layer and a mixture of BIO-PSA 7-4301 and BIO-PSA 7-4201 in a ratio of 70:30 in the outer phase of the additional rotigotine-containing skin contact layer.

BIO-PSA 7-4301 has a solution viscosity at 25° C. and about 60% solids content in heptane of 500 mPa s and a complex viscosity at 0.01 rad/s at 30° C. of $5\times10^6$ Poise. BIO-PSA 7-4201 has a solution viscosity at 25° C. and about 60% solids content in heptane of 450 mPa s and a complex viscosity at 0.01 rad/s at 30° C. of $1\times10^8$ Poise. BIO-PSA 7-4302 has a solution viscosity at 25° C. and about 60% solids content in ethyl acetate of 1200 mPa s and a complex viscosity at 0.01 rad/s at 30° C. of $5\times10^6$ Poise. BIO-PSA 7-4202 has a solution viscosity at 25° C. and about 60% solids content in heptane of 800 mPa s and a complex viscosity at 0.01 rad/s at 30° C. of $1\times10^8$ Poise.

Inner Phase

In order to provide the desired permeation rate of rotigotine base, a polymer mixture is present in the inner phase comprising at least two hydrophilic polymers selected from at least two of the polymer groups:

polyvinylpyrrolidones having a K-Value of at least 80, or from 80 to 200, polyvinylpyrrolidones having a K-Value of less than 80, or from 10 to 79, copolymers of vinyl caprolactam, vinylacetate and ethylene glycol, copolymers of vinylpyrrolidone and vinylacetate, copolymers of ethylene and vinylacetate, polyethylene glycols, polypropylene glycols, acrylic polymers, modified celluloses.

In accordance with a certain embodiment of the invention, the at least two hydrophilic polymers are selected from at least two of the polymer groups:

polyvinylpyrrolidones having a K-Value of at least 80, or from 80 to 200, polyvinylpyrrolidones having a K-Value of less than 80, or from 10 to 79, copolymers of vinyl caprolactam, vinylacetate and ethylene glycol, copolymers of vinylpyrrolidone and vinylacetate, copolymers of ethylene and vinylacetate, polyethylene glycols, polypropylene glycols, copolymers of dimethylaminoethyl methacrylate, butyl methacrylate and methyl methacrylat, copolymers of methacrylic acid and methyl methacrylat, hydroxypropyl methylcellulose, hydroxypropyl methylcellulose acetate succinates.

In accordance with a certain embodiment of the invention the polymer mixture in the inner phase comprises two hydrophilic polymers in a ratio of 1:1 to about 1:10, or 1:1 to about 1:4, or 1:1 to about 1:2.

According to a certain embodiment the polymer mixture in the inner phase comprises at least polyvinylpyrrolidone having a K-Value of at least 80, or from 80 to 200, which is preferably present in the same or in a smaller amount than the at least one further hydrophilic polymer.

In accordance with a certain embodiment of the invention the rotigotine-containing biphasic layer contains polyvinylpyrrolidone having a K-Value of at least 80, or from 80 to 200, preferably in an amount of about 0.1 mg/cm$^2$ to about 5 mg/cm$^2$, preferably of about 0.1 mg/cm$^2$ to about 1.5 mg/cm$^2$, more preferably of about 0.5 mg/cm$^2$ to about 0.7 mg/cm$^2$, or of about 1% to about 20%, preferably of about 1% to about 10%, more preferably of about 3% to about 5% of the biphasic layer.

In accordance with a certain specific embodiment of the invention the polymer mixture in the inner phase comprises polyvinylpyrrolidone having a K-Value of at least 80, or from 80 to 200, in particular 90, and polyvinylpyrrolidone having a K-Value of less than 80, or from 10 to 79, in particular 30. The ratio of polyvinylpyrrolidone having a K-Value of at least 80, or from 80 to 200, to polyvinylpyrrolidone having a K-Value of less than 80, or from 10 to 79, may be 4:1 to 1:4, or 2:1 to 1:2, or 1:1 to 1:2.

In accordance with a certain embodiment of the invention the rotigotine-containing biphasic layer contains polyvinylpyrrolidone having a K-Value of less than 80, or from 10 to 79, preferably in an amount of about 0.1 mg/cm$^2$ to about 5 mg/cm$^2$, preferably of about 0.1 mg/cm$^2$ to about 1.5 mg/cm$^2$, more preferably of about 0.5 mg/cm$^2$ to about 1.0 mg/cm$^2$, or of about 1% to about 20%, preferably of about 1% to about 10%, of about 5% to about 7% of the biphasic layer.

In accordance with a certain embodiment of the invention the rotigotine-containing biphasic layer contains polyvinylpyrrolidone having a K-Value of at least 80, or from 80 to 200, in an amount of about 0.5 mg/cm$^2$ to about 0.7 mg/cm$^2$ and polyvinylpyrrolidone having a K-Value of less than 80, or from 10 to 79 in an amount of about 0.5 mg/cm$^2$ to about 1.0 mg/cm$^2$.

According to a certain embodiment of the invention, the ratio of rotigotine base to the polymer mixture in the inner phase is 1:0.2 to 1:1, preferably 1:0.2 to 1:0.8, or more preferably 1:0.4 to 1:0.6.

According to a certain embodiment, the ratio of rotigotine base to polyvinylpyrrolidone having a K-Value of at least 80, or from 80 to 200, is 1:0.1 to 1:0.5, preferably 1:0.1 to 1:0.3. The ratio of rotigotine base to polyvinylpyrrolidone having a K-Value of less than 80, or from 10 to 79 may be 1:0.1 to 1:0.5, preferably 1:0.2 to 1:0.4.

According to a certain embodiment the ratio of rotigotine base to polyvinylpyrrolidone having a K-Value of at least 80, or from 80 to 200, and polyvinylpyrrolidone having a K-Value of less than 80, or from 10 to 79 is about 1:0.2:0.3.

The polyvinylpyrrolidone having a K-Value of less than 80, or from 10 to 79, may be a polyvinylpyrrolidone having a K-Value range of 25 to 35, or a nominal K-Value of 30, or a K-Value of less than 25, or a nominal K-Value of 17, or a nominal K-Value of 12. The polyvinylpyrrolidone having a K-Value of at least 80, or from 80 to 200, may be a polyvinylpyrrolidone having a K-Value range of 85 to 95, or a nominal K-Value of 90.

According to a certain embodiment the polymer mixture in the inner phase comprises polyvinylpyrrolidone having a nominal K-Value of 90 and polyvinylpyrrolidone having a nominal K-Value of 30, preferably in a ratio of 1:1.4, or 1:1.5.

Skin Contact Layer

The TTS in accordance with the invention may comprise an additional skin contact layer which is an adhesive layer.

According to a certain embodiment, the additional skin contact layer has a pressure-sensitive adhesive composition comprising pressure-sensitive polymers selected from polysiloxanes, polyisobutylenes, polyacrylates, a copolymer of styrene and butadiene, a copolymer of styrene and isoprene, or a mixture thereof. A pressure-sensitive adhesive composition comprising pressure-sensitive adhesive polysiloxane(s) is preferred according to a certain embodiment of the invention.

The additional skin contact layer may be manufactured active agent-free or active agent-containing. For an active agent-free skin contact layer an area weight of about 5 g/m$^2$ to about 60 g/m$^2$ is preferred.

According to a certain embodiment, the additional skin contact layer is manufactured containing rotigotine base and preferably has an area weight of about 10 g/m$^2$ to about 150 g/m$^2$.

According to a certain embodiment, rotigotine base is present in the additional skin contact layer in a smaller amount than in the rotigotine-containing biphasic layer. Rotigotine base may be present in the additional skin contact layer in an amount of 1% to 15%, or of less than 9%, or from 1% to 8% of said skin contact layer. Preferably the additional skin contact layer comprises 1% to 8% rotigotine and has an area weight of about 10 g/m$^2$ to about 150 g/m$^2$. A reduced active agent content (e.g. an amount of less than 9% rotigotine base) in the skin contact layer is in particular advantageous with respect to sufficient skin tolerability and sufficient tack.

According to a certain embodiment of the invention the additional skin contact layer comprises in the inner phase polyvinylpyrrolidone having a K-Value of at least 80, or from 80 to 200. The ratio of rotigotine base and polyvinylpyrrolidone having a K-Value of at least 80, or from 80 to 200, in the skin contact layer may be from about 1:0.2 to about 1:1, preferably from about 1:0.3 to about 1:0.5.

According to a certain embodiment of the invention the ratio of rotigotine base to the polymer mixture in the biphasic layer is 1:0.4 to 1:0.6 and the ratio of rotigotine base to polyvinylpyrrolidone having a K-Value of at least 80, or from 80 to 200 in the skin contact layer is 1:0.2 to 1:0.5.

According to a certain embodiment, the additional skin contact layer differs from the rotigotine-containing biphasic layer but is also in the form of the rotigotine-containing biphasic layer, the biphasic layer having
a) an outer phase having a composition comprising 75% to 100% of a polymer or a polymer mixture, and
b) an inner phase having a composition comprising rotigotine base,
wherein the inner phase forms dispersed deposits in the outer phase, and
wherein the inner phase comprises
i. rotigotine base, and
ii. at least one hydrophilic polymer,
wherein the at least one hydrophilic polymer in the inner phase is present in an amount sufficient so that said rotigotine base forms a solid solution with the at least one hydrophilic polymer,
optionally wherein the at least one hydrophilic polymer is a polymer mixture comprising at least two hydrophilic polymers.

According to a certain embodiment of the invention, the additional skin contact layer is also in the form of the rotigotine-containing biphasic layer and comprises in the inner phase polyvinylpyrrolidone having a K-Value of at least 80, or from 80 to 200. The ratio of rotigotine base and polyvinylpyrrolidone having a K-Value of at least 80, or from 80 to 200, in the skin contact layer may be from about 1:0.2 to about 1:1, preferably from about 1:0.3 to about 1:0.5.

According to a certain specific embodiment, the additional rotigotine-containing skin contact layer is also in the form of a biphasic layer having
a) an outer phase having a pressure-sensitive adhesive composition comprising 75% to 100% of pressure-sensitive adhesive polysiloxanes, and
b) an inner phase having a composition comprising rotigotine base,
wherein the inner phase forms dispersed deposits in the outer phase, and
wherein the inner phase comprises
i. from 1% to 8% rotigotine base of said skin contact layer, and
ii. polyvinylpyrrolidone having a K-Value of at least 80, or from 80 to 200, wherein said polyvinylpyrrolidone is present in an amount sufficient so that said amount of rotigotine base forms a solid solution with said polyvinylpyrrolidone,
wherein the skin contact layer has an area weight of about 10 $g/m^2$ to about 150 $g/m^2$.

Release Characteristic

In accordance with the invention, the TTS is further characterized by the rotigotine permeation rate determined by in vitro experiments carried out with an in vitro rotigotine permeation test. The rotigotine permeation was evaluated by a membrane permeation test performed over an extended period of time using a 51 µm thick membrane consisting of an ethylene vinyl acetate (EVA) copolymer with 9% vinyl acetate (CoTran™ Membrane, 3M) and the Paddle over Disk apparatus described in the United States Phamacopeia (USP). Phosphate buffer pH 4.5 was used as acceptor medium (900 ml; 32° C.; 50 rpm).

Example formulations with an area of 10 $cm^2$ are punched from laminates. The rotigotine permeation rates into the acceptor medium were determined in regular intervals using a validated UV photometric or HPLC method.

According to certain embodiments, the TTS provides a permeation rate of rotigotine base as measured through an EVA membrane in a 4 hours time interval from hour 8 to hour 12 that is therapeutically effective, preferably of at least 10.5 $\mu g/cm^2/hr$ to about 15 $\mu g/cm^2/hr$, more preferably of at least 11 $\mu g/cm^2/hr$ to about 15 $\mu g/cm^2/hr$.

According to certain embodiments, the TTS provides a permeation rate of rotigotine base as measured through an EVA membrane in 4 hours, or 6 hours time intervals from 24 hours to 168 hours that is constant within 20% points, preferably within 15% points, more preferably within 10% points from 24 hours to 168 hours.

According to a specific aspect of the invention, the TTS for the transdermal administration of rotigotine provides a permeation rate of rotigotine base
(a) of at least 11 fig/$cm^2$/hr to about 15 $\mu g/cm^2/hr$ as measured through an EVA membrane in a 4 hours time interval from hour 8 to hour 12, and
(b) which is constant within 20% points from 24 hours to 168 hours when measured through an EVA membrane in 4 hours time intervals from 24 hours to 168 hours.

In accordance with the invention, the rotigotine skin permeation was evaluated by a membrane permeation test performed over an extended period of time using dermatomized human skin of about 300 µm thickness in a flow cell setup. A phosphate buffered saline (PBS) pH 6.2 was used as acceptor medium (32° C.).

Method of Treatment/Medical Use

According to one aspect, the transdermal therapeutic system in accordance with the invention and as described above in detail is for use in a method of treatment, in particular for use in a method of treating patients suffering from Parkinson's disease, Parkinson's plus syndrome, depression, anxiety, AHDS, fibromyalgia, the restless-legs syndrome and for use in the treatment or prevention of dopaminergic neuron loss or the treatment or prevention of cognitive disorders, dementia or lewy body disease.

The method comprises in particular the application of the TTS for about 168 hours (corresponding to 7 days or one week) on the skin of a human patient. According to other methods in accordance with the invention the TTS can be applied for at least 24 hours (1 day), or about 72 hours (3 days), or about 96 hours (4 days) on the skin of a human patient. A 168 hour (7 day)-application is preferred.

The TTS according to the invention is in particular for use in a method of treatment by applying a transdermal therapeutic system for about 168 hours (corresponding to 7 days or one week) on the skin of a human patient. According to other aspects of the invention, the TTS is for use in a method of treatment by applying a transdermal therapeutic system for at least 24 hours (1 day), or about 72 hours (3 days), or about 96 hours (4 days) on the skin of a human patient. A 168 hour (7 day)-application is preferred.

According to certain embodiments of the invention, therapeutically effective amounts of rotigotine base are provided for 1 to 7 days by said transdermal therapeutic system during an administration period of 1 to 7 days.

A multi-day TTS according to the invention has the advantage of allowing for a reduced application frequency compared to daily applied transdermal therapeutic systems. This is particularly advantageous for patients suffering from severe dopaminergic disorders, like Parkinson's disease, as these patients often experience motor disabilities which make the frequent handling and administration of transdermal therapeutic systems difficult. At the same time, the number of skin application sites to be treated with transdermal therapeutic systems during a long-term medication is reduced. A prolongation of the medication interval e.g. from 1 day to at least 3 or even at least 7 days minimizes the potential risk of skin lesions associated with frequent TTS stripping from the patients' skin at skin application sites selected for repeated TTS administration. E.g., for the once-daily TTS Neupro® 14 different skin application sites are necessary for repeated TTS application to avoid skin irritation, whereas with a once-weakly TTS only 3 skin application sites are necessary. In addition, the influence of inter- and intra-individually differing lag-times on the absorption of rotigotine, which may be associated with the daily replacement of rotigotine-containing transdermal therapeutic systems in the case of low skin permeability and which may cause therapeutically unwanted fluctuations of the plasma levels of rotigotine, can be eliminated by the multi-day TTS of the present invention. Finally, the replacement of a daily TTS administration by one single administration for several days, for example by an administration once or twice weekly, contributes to the reduction of the costs of the respective medication by saving material and production time.

According to certain embodiments of the invention, therapeutically effective amounts of rotigotine base are provided for 3 days by the transdermal therapeutic system according to the invention during an administration period of 3 days, preferably for 4 days during an administration period of 4 days, or for 7 days during an administration period of 7 days.

Method of Manufacture

According to one further aspect, the invention relates to a method of manufacture of a transdermal therapeutic system for the transdermal administration of rotigotine, comprising the steps of:
(1) preparing a rotigotine-containing biphasic coating mixture having an inner phase dispersed in an outer phase,
(2) coating said rotigotine-containing biphasic coating mixture on a film in an amount to provide a layer with a coating weight,
(3) drying said coated layer to provide a dried layer with a coating weight to provide a rotigotine-containing dried biphasic layer with the desired area weight,
(4) optionally laminating two or more of said dried layers to provide a rotigotine-containing dried biphasic layer with the desired area weight,
(5) laminating said rotigotine-containing dried biphasic layer to a backing layer,
(6) optionally laminating said rotigotine-containing dried biphasic layer to an additional skin contact layer.

According to a certain embodiment of the invention, a pressure-sensitive adhesive mixture of pressure-sensitive adhesive polysiloxanes in heptane or ethyl acetate is used for the production of the biphasic layer and optionally the additional skin contact layer.

The preparation of the rotigotine-containing biphasic coating mixture may comprise the steps of:
(1) mixing a polymer mixture comprising at least two hydrophilic polymers selected from at least two of the polymer groups:
polyvinylpyrrolidones having a K-Value of at least 80, or from 80 to 200,
polyvinylpyrrolidones having a K-Value of less than 80, or from 10 to 79,
copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
acrylic polymers,
modified celluloses,
with a solvent to obtain a solution,
(2) optionally adding tocopherol, ascorbyl palmitate, and an aqueous sodium metabisulfite solution to the solution of step 1,
(3) adding rotigotine base and a mixture of a composition comprising 75% to 100% of a polymer or a polymer mixture in a solvent to said solution to provide a rotigotine-containing biphasic coating mixture.

Useful solvents for dissolving the polymer mixture comprising at least two hydrophilic polymers are alcohols (e.g. ethanol), acetone and methyl ethyl ketone, or mixtures thereof, ethanol is preferred. The composition comprising 75% to 100% of a polymer or a polymer mixture may be dissolved in heptanes, hexanes, toluene, or ethyl acetate, preferably in heptane or ethyl acetate.

According to a certain embodiment of the invention, the preparation of the rotigotine-containing biphasic coating mixture comprises the steps of:
(1) mixing a polymer mixture comprising at least two hydrophilic polymers selected from at least two of the polymer groups:
polyvinylpyrrolidones having a K-Value of at least 80, or from 80 to 200,
polyvinylpyrrolidones having a K-Value of less than 80, or from 10 to 79,
copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
acrylic polymers,
modified celluloses,
with a solvent to obtain a solution,
(2) optionally adding tocopherol, ascorbyl palmitate, and an aqueous sodium metabisulfite solution to the solution of step 1,
(3) adding rotigotine base to said solution to obtain a rotigotine-containing mixture,
(4) adding a mixture of a composition comprising 75% to 100% of a polymer or a polymer mixture in a solvent to said rotigotine-containing mixture to provide a rotigotine-containing biphasic coating mixture.

Useful solvents for the composition comprising 75% to 100% of a polymer or a polymer mixture described in the previous paragraph are heptanes, hexanes, or toluene, n-heptane is preferred.

According to a certain embodiment of the invention, the preparation of the rotigotine-containing biphasic coating mixture comprises the steps of:
(1) mixing a polymer mixture comprising at least two hydrophilic polymers selected from at least two of the polymer groups:
   polyvinylpyrrolidones having a K-Value of at least 80, or from 80 to 200,
   polyvinylpyrrolidones having a K-Value of less than 80, or from 10 to 79,
   copolymers of vinyl caprolactam, vinylacetate and ethylene glycol,
   copolymers of vinylpyrrolidone and vinylacetate,
   copolymers of ethylene and vinylacetate,
   polyethylene glycols,
   polypropylene glycols,
   acrylic polymers,
   modified celluloses,
   with a solvent to obtain a solution,
(2) optionally adding tocopherol, ascorbyl palmitate, and an aqueous sodium metabisulfite solution to the solution of step 1,
(3) adding a mixture of a composition comprising 75% to 100% of a polymer or a polymer mixture in a solvent to said solution,
(4) adding rotigotine base to said mixture to provide a rotigotine-containing biphasic coating mixture.

Preferred solvents for dissolving the polymer mixture comprising at least two hydrophilic polymers described in the previous paragraph are alcohols (e.g. ethanol). A preferred solvent for the composition comprising 75% to 100% of a polymer or a polymer mixture described in the previous paragraph is ethyl acetate.

According to certain embodiments, moderate heating to about 40° C. up to about 60° C. may be useful when adding rotigotine base in any one of the preparation methods for the rotigotine-containing biphasic coating mixture described in the previous paragraphs.

According to a certain embodiment of the invention, the rotigotine-containing biphasic layer is laminated to an additional skin contact layer and wherein the preparation of the skin contact layer comprises the steps of:
(1) providing an adhesive coating mixture, preferably a rotigotine-containing biphasic coating mixture having an inner phase dispersed in an outer phase and comprising at least one hydrophilic polymer in the inner phase,
(2) coating said adhesive coating mixture on a film to provide a layer of said adhesive coating mixture,
(3) drying said coated layer to provide a dried layer with a coating weight to provide said skin contact layer with the desired area weight,
(4) optionally laminating two or more of said dried layers to provide said skin contact layer with the desired area weight.

EXAMPLES

The present invention will now be more fully described with reference to the accompanying examples. It should be understood, however, that the following description is illustrative only and should not be taken in any way as a restriction of the invention.

Comparative Example 1

The composition of the rotigotine-containing biphasic coating mixture is summarized in Table 1 below.

TABLE 1

| Excipients | Solid [%] | Solution [%] |
|---|---|---|
| Ethanol | — | 10.750 |
| Polyvinylpyrrolidone (Kollidon 90 F) | 8.000 | 4.560 |
| Sodium metabisulfite solution 10% (w/w) | 0.0036 | 0.020 |
| Ascorbyl palmitate | 0.0401 | 0.0228 |
| all-rac-Tocopherol | 0.0994 | 0.0566 |
| Rotigotine | 18.00 | 10.260 |
| BIO PSA 7-4302 (60%) | 36.93 | 35.080 |
| BIO PSA 7-4202 (60%) | 36.93 | 35.080 |
| Ethyl acetate | — | 4.175 |
| Total | 100.00 | 100.00 |
| Solids content | | 57.0% |

Preparation of the Rotigotine-Containing Biphasic Coating Mixture (Step 1):

To a solution of 13.68 g polyvinylpyrrolidone (PVP, Kollidon 90F) in 32.23 g ethanol and 12.52 g ethyl acetate, 0.171 g DL-α-tocopherol, 0.068 g ascorbyl palmitate and 0.062 g of an aqueous sodium metabisulfite solution (10% by weight) were added and mixed to obtain a clear solution (1000 rpm, propeller stirrer). 105.24 g silicone adhesive BIO-PSA 7-4202 (60% by weight in ethyl acetate) and 105.24 g silicone adhesive BIO-PSA 7-4302 (60% by weight in ethyl acetate) were added to the obtained PVP solution and stirred at 500 rpm until complete mixing. 30.78 g rotigotine of polymorphic Form II were added while stirring. The mixture was heated up to 40° C. and stirred at 500 rpm for a minimum of 60 min until a homogenous dispersion was obtained.

Preparation of the Transdermal Therapeutic System (TTS) (Step 2):

The mixture obtained in step 1 was coated onto two sheets of a suitable polyester release liner (e.g. Scotchpak™ 9755). The coated release liner sheets were placed in a drying oven and dried at 50° C. for about 30 min and then at 115° C. for about 10 min. The coating thickness was chosen such that removal of the solvents results in a coating weight of each of the two rotigotine-containing layers of 75 g/m². The first rotigotine-containing layer was laminated with (1) a polyester-type backing foil and (2) the second rotigotine-containing layer after removal of the release liner from the surface of the first layer to provide the rotigotine-containing self-adhesive layer structure with a rotigotine-containing biphasic layer having an area weight of 150 g/m². Finally, individual systems (TTS) having a size of 10 cm² were punched out of the rotigotine-containing self-adhesive layer structure and sealed into pouches.

Comparative Example 2

The composition of the rotigotine-containing biphasic coating mixture is summarized in Table 2 below.

TABLE 2

| Excipients | Solid [%] | Solution [%] |
|---|---|---|
| Ethanol | — | 5.56 |
| Acetone | — | 5.64 |
| Polyvinylpyrrolidone (Kollidon 30) | 12.00 | 8.33 |
| Rotigotine | 18.00 | 12.50 |
| Sodium metabisulfite solution 10% (w/w) | 0.0054 | 0.0375 |
| Ascorbyl palmitate | 0.040 | 0.03 |
| all-rac-Tocopherol | 0.10 | 0.07 |
| BIO PSA 7-4301 (71.5%) | 34.93 | 33.92 |
| BIO PSA 7-4201 (71.5%) | 34.93 | 33.92 |
| Total | 100.00 | 100.00 |
| Solids content | — | 69.4% |

Preparation of the Rotigotine-Containing Biphasic Coating Mixture (Step 1):

38.90 g polyvinylpyrrolidone (PVP, Kollidon 30), 0.324 g DL-α-Tocopherol, 0.130 g ascorbyl palmitate and 0.175 g of an aqueous sodium metabisulfite solution (10% by weight) were mixed with 25.93 g anhydrous ethanol to obtain a clear solution (300-2000 rpm, propeller stirrer). 26.32 g acetone and 58.32 g rotigotine of polymorphic Form II were added while stirring at 300 rpm and heated to 40° C. for 60 min. 158.36 g silicone adhesive BIO-PSA 7-4201 (71.5% by weight in n-heptane) and 158.36 g silicone adhesive BIO-PSA 7-4301 (71.5% by weight in n-heptane) were added to the obtained solution of rotigotine, PVP and antioxidants and stirred at 2000 rpm for 10 min (turbine stirrer).

Preparation of the Transdermal Therapeutic System (TTS) (Step 2):

The mixture obtained in step 1 was coated onto two sheets of a suitable polyester release liner (e.g. Scotchpak™ 9755). The coated release liner sheets were placed in a drying oven and dried at 50° C. for about 30 min and then at 110° C. for about 10 min. The coating thickness was chosen such that removal of the solvents results in a coating weight of each of the rotigotine-containing layers of 75 g/m². The first rotigotine-containing layer was laminated with (1) a polyester-type backing foil and (2) the second rotigotine-containing layer after removal of the release liner from the surface of the first layer to provide the rotigotine-containing self-adhesive layer structure with a rotigotine-containing biphasic layer having an area weight of 150 g/m². Finally, individual systems (TTS) having a size of 10 cm² were punched out of the rotigotine-containing self-adhesive layer structure and sealed into pouches.

Example 1

The composition of the rotigotine-containing biphasic coating mixtures is summarized in Table 3 below.

TABLE 3

| Excipients | Solid [%] | Solution [%] |
|---|---|---|
| Ethanol | — | 19.24 |
| Polyvinylpyrrolidone (Kollidon 90F) | 4.0 | 2.28 |
| Polyvinylpyrrolidone (Kollidon 30) | 5.5 | 3.13 |
| Sodium metabisulfite solution 10% (w/w) | 0.0043 | 0.02 |

TABLE 3-continued

| Excipients | Solid [%] | Solution [%] |
|---|---|---|
| Ascorbyl palmitate | 0.04 | 0.02 |
| all-rac-Tocopherol | 0.099 | 0.06 |
| Rotigotine | 18.00 | 10.26 |
| BIO PSA 7-4301 (71.5%) | 36.18 | 28.84 |
| BIO PSA 7-4201 (71.5%) | 36.18 | 28.84 |
| n-heptane | — | 7.31 |
| Total | 100.00 | 100.00 |
| Solids content | | 57% |

Preparation of the Rotigotine-Containing Biphasic Coating Mixture (Step 1):

3.31 g polyvinylpyrrolidone (PVP, Kollidon 90F), 4.54 g PVP (Kollidon 30), 0.087 g DL-α-Tocopherol, 0.029 g ascorbyl palmitate and 0.029 g of an aqueous sodium metabisulfite solution (10% by weight) were mixed with 27.92 g anhydrous ethanol to obtain a clear solution (1000 rpm, propeller stirrer). 14.89 g rotigotine of polymorphic Form II were added while stirring at 60 rpm at 60° C. for 60 min with a propeller stirrer. 41.84 g silicone adhesive BIO-PSA 7-4201 (71.5% by weight in n-heptane), 41.84 g silicone adhesive BIO-PSA 7-4301 (71.5% by weight in n-heptane) and 10.61 g n-heptane were added to the obtained solution of rotigotine, PVP and antioxidants and stirred at 1000 rpm for 10 min (dissolver stirrer).

Preparation of the Transdermal Therapeutic System (TTS) (Step 2):

The mixture obtained in step 1 was coated onto sheets of a suitable polyester release liner (e.g. Scotchpak™ 9755). The coated release liner sheets were placed in a drying oven and dried at 50° C. for about 30 min and then at 110° C. for about 10 min. The coating thickness was chosen such that removal of the solvents results in a coating weight of the rotigotine-containing biphasic layer of 150 g/m². The rotigotine-containing biphasic layer was laminated with a polyester-type backing foil to provide the rotigotine-containing self-adhesive layer structure. Finally, individual systems (TTS) having a size of 10 cm² were punched out of the rotigotine-containing self-adhesive layer structure and sealed into pouches.

Example 2a

The compositions of the rotigotine-containing biphasic coating mixtures are summarized in Table 4 below.

TABLE 4

| | Mixture 1 | | Mixture 2 | |
|---|---|---|---|---|
| Excipients | solid [%] | solution [%] | solid [%] | solution [%] |
| Ethanol | — | 21.40 | — | 14.02 |
| Polyvinylpyrrolidone (Kollidon 90F) | 4.44 | 2.53 | 3.33 | 2.07 |
| Polyvinylpyrrolidone (Kollidon 30) | 6.11 | 3.48 | — | — |
| Sodium metabisulfite solution 10% (w/w) | 0.0048 | 0.03 | 0.015 | 0.01 |
| Ascorbyl palmitate | 0.04 | 0.02 | 0.02 | 0.01 |
| all-rac-Tocopherol | 0.11 | 0.06 | 0.04 | 0.02 |
| Rotigotine | 20.00 | 11.40 | 7.5 | 4.67 |
| BIO PSA 7-4301 (70%) | 20.79 | 16.93 | 62.38 | 55.43 |

TABLE 4-continued

|  | Mixture 1 | | Mixture 2 | |
| --- | --- | --- | --- | --- |
| Excipients | solid [%] | solution [%] | solid [%] | solution [%] |
| BIO PSA 7-4201 (70%) | 48.50 | 39.49 | 26.73 | 23.76 |
| n-heptane | — | 4.65 | — | 0.00 |
| Total | 100.00 | 100.00 | 100.00 | 100.00 |
| Solids content | | 57% | | 62.2% |

Preparation of Rotigotine-Containing Biphasic Coating Mixture 1 (Step 1):

8.00 g polyvinylpyrrolidone (PVP, Kollidon 90F), 10.99 g PVP (Kollidon 30), 0.198 g DL-α-Tocopherol, 0.080 g ascorbyl palmitate and 0.086 g of an aqueous sodium metabisulfite solution (10% by weight) were mixed with 35.72 g anhydrous ethanol to obtain a clear solution (1000 rpm, propeller stirrer). 36.00 g rotigotine of polymorphic Form II and 31.76 g anhydrous ethanol were added while stirring at 60 rpm at 60° C. for 60 min with a propeller stirrer. 124.73 g silicone adhesive BIO-PSA 7-4201 (70% by weight in n-heptane), 53.43 g silicone adhesive BIO-PSA 7-4301 (70% by weight in n-heptane) and 14.76 g n-heptane were added to the obtained solution of rotigotine, PVP and antioxidants and stirred at 2000 rpm for 5 min (dissolver stirrer).

Preparation of Rotigotine-Containing Biphasic Coating Mixture 2 (Step 2):

3.33 g PVP (Kollidon 90F), 0.040 g DL-α-Tocopherol, 0.020 g ascorbyl palmitate and 0.015 g of an aqueous sodium metabisulfite solution (10% by weight) were mixed with 22.54 g anhydrous ethanol to obtain a clear solution (1000 rpm, propeller stirrer). 7.50 g rotigotine of polymorphic Form II were added while stirring at 60 rpm and heated to 60° C. for 60 min. 38.19 g silicone adhesive BIO-PSA 7-4201 (70% by weight in n-heptane) and 89.11 g silicone adhesive BIO-PSA 7-4301 (70% by weight in n-heptane) were added to the obtained solution of rotigotine, PVP and antioxidants and stirred at 2000 rpm for 5 min (dissolver stirrer).

Preparation of the Transdermal Therapeutic System (TTS) (Step 3):

Mixture 1 obtained in step 1 was coated onto sheets of a suitable polyester release liner (e.g. Scotchpak™ 9755). The coated release liner sheets were placed in a drying oven and dried at 50° C. for about 30 min and then at 110° C. for about 10 min. The coating thickness was chosen such that removal of the solvents results in a coating weight of the first rotigotine-containing biphasic layer of 122 g/m². The rotigotine-containing biphasic layer was laminated with a polyester-type backing foil. Mixture 2 obtained in step 2 was coated onto sheets of a suitable polyester release liner (e.g. Scotchpak™ 9755). The coated release liner sheets were placed in a drying oven and dried at 50° C. for about 30 min and then at 110° C. for about 10 min. The coating thickness was chosen such that removal of the solvents results in a coating weight of the second rotigotine-containing biphasic layer of 35 g/m² to provide a rotigotine-containing skin contact layer. The rotigotine-containing skin contact layer was laminated with the first rotigotine-containing biphasic layer after removal of the release liner from the surface of the rotigotine-containing biphasic layer to provide the rotigotine-containing self-adhesive layer structure with a rotigotine-containing biphasic layer and rotigotine-containing skin contact layer having a total area weight of 157 g/m². Finally, individual systems (TTS) having a size of 10 cm² were punched out of the rotigotine-containing self-adhesive layer structure and sealed into pouches.

Example 2b

The composition of the rotigotine-containing biphasic mixtures and the method of manufacture were as described for Example 2a. For the preparation of the transdermal therapeutic system (TTS) the coating thickness was chosen such that removal of the solvents results in a coating weight of the first rotigotine-containing biphasic layer of 112 g/m² and of the second rotigotine-containing biphasic layer providing the rotigotine-containing skin contact layer of 60 g/m².

Example 3

In Example 3, the in-vitro rotigotine permeation of Comparative Examples 1 and 2 and Examples 1, 2a and 2b was evaluated by a membrane permeation test performed over 192 hours using a 51 μm thick membrane consisting of an ethylene vinyl acetate (EVA) copolymer with 9% vinyl acetate (CoTran™ Membrane, 3M) and the Paddle over Disk apparatus described in the United States Phamacopeia (USP). Phosphate buffer pH 4.5 was used as acceptor medium (900 ml; 32° C.; 50 rpm). TTS with an area of 10 cm² of Comparative Example 1 were tested against TTS of Comparative Example 2 and Examples 1, 2a and 2b. The permeation of rotigotine into the acceptor medium was determined by HPLC. The results are shown in Tables 5 to 7 and FIGS. 1 to 4.

TABLE 5

| | rotigotine permeation [μg/cm²] n = 3 (SD) | | |
| --- | --- | --- | --- |
| Time [h] | Comparative Example 1 | Comparative Example 2 | Example 1 |
| 0 | 0.00 (0.00) | 0.00 (0.00) | 0.00 (0.00) |
| 4 | 37.27 (4.40) | 20.36 (1.05) | 25.22 (8.65) |
| 8 | 82.49 (7.09) | 51.39 (1.58) | 65.67 (8.87) |
| 12 | 128.82 (4.17) | 88.77 (1.88) | 110.66 (8.51) |
| 16 | 183.90 (2.07) | 130.07 (2.70) | 158.14 (7.90) |
| 20 | 235.10 (2.48) | 174.05 (3.67) | 207.12 (7.94) |
| 24 | 287.11 (2.31) | 219.68 (5.22) | 257.40 (8.15) |
| 28 | 339.69 (2.26) | 265.60 (6.01) | 308.05 (9.60) |
| 32 | 392.64 (1.98) | 312.27 (6.06) | 358.92 (10.09) |
| 36 | 445.75 (1.95) | 359.56 (6.37) | 410.66 (9.75) |
| 40 | 498.61 (1.63) | 407.46 (6.54) | 462.72 (9.59) |
| 44 | 551.23 (1.58) | 456.26 (7.24) | 516.01 (9.27) |
| 48 | 602.71 (1.72) | 505.57 (8.91) | 568.43 (10.91) |

TABLE 5-continued

| | rotigotine permeation [μg/cm²] n = 3 (SD) | | |
|---|---|---|---|
| Time [h] | Comparative Example 1 | Comparative Example 2 | Example 1 |
| 52 | 656.10 (1.77) | 554.98 (9.60) | 621.21 (13.25) |
| 56 | 709.57 (2.04) | 604.41 (9.36) | 674.16 (13.81) |
| 60 | 762.62 (2.69) | 653.68 (10.02) | 726.83 (13.91) |
| 64 | 815.21 (3.78) | 703.31 (10.51) | 779.97 (14.46) |
| 68 | 867.34 (4.32) | 752.84 (11.05) | 832.92 (15.86) |
| 72 | 919.19 (5.34) | 802.56 (11.98) | 886.01 (17.68) |
| 76 | 969.86 (5.59) | 852.21 (12.44) | 938.53 (20.82) |
| 80 | 1021.38 (6.16) | 901.45 (12.88) | 991.09 (22.34) |
| 84 | 1073.09 (6.43) | 950.78 (13.81) | 1043.93 (23.96) |
| 88 | 1123.22 (7.52) | 1000.01 (13.87) | 1096.25 (25.38) |
| 92 | 1172.30 (8.19) | 1048.38 (14.83) | 1149.06 (27.35) |
| 96 | 1221.74 (9.81) | 1097.35 (15.66) | 1201.29 (30.20) |
| 100 | 1271.46 (10.86) | 1145.63 (15.79) | 1253.78 (32.38) |
| 104 | 1320.81 (11.32) | 1195.13 (17.12) | 1305.28 (34.31) |
| 108 | 1369.46 (12.72) | 1244.23 (17.91) | 1357.97 (36.94) |
| 112 | 1415.27 (13.63) | 1292.56 (18.54) | 1410.03 (39.14) |
| 116 | 1460.86 (13.10) | 1340.48 (18.65) | 1462.18 (41.14) |
| 120 | 1507.33 (14.18) | 1388.94 (20.65) | 1513.86 (43.45) |
| 124 | 1553.71 (15.26) | 1436.16 (21.45) | 1564.08 (46.46) |
| 128 | 1600.48 (16.81) | 1483.73 (21.60) | 1615.67 (48.18) |
| 132 | 1646.49 (17.41) | 1531.36 (22.62) | 1667.11 (50.99) |
| 136 | 1691.47 (19.29) | 1578.73 (24.12) | 1718.03 (53.38) |
| 140 | 1736.65 (20.78) | 1625.11 (24.23) | 1768.82 (56.89) |
| 144 | 1780.74 (21.97) | 1671.40 (24.31) | 1818.88 (60.06) |
| 148 | 1825.03 (22.41) | 1717.44 (26.45) | 1869.09 (63.35) |
| 152 | 1869.91 (24.75) | 1763.33 (27.23) | 1919.03 (66.93) |
| 156 | 1914.56 (25.78) | 1809.14 (26.56) | 1969.55 (70.08) |
| 160 | 1958.29 (26.57) | 1854.77 (28.18) | 2018.80 (73.12) |
| 164 | 2000.87 (27.32) | 1899.04 (28.95) | 2068.86 (76.86) |
| 168 | 2045.11 (28.02) | 1945.01 (29.61) | 2118.35 (80.33) |
| 172 | 2087.75 (29.56) | 1988.21 (30.39) | 2167.52 (84.41) |
| 176 | 2130.92 (30.79) | 2031.89 (30.95) | 2215.72 (87.72) |
| 180 | 2174.24 (32.05) | 2074.08 (30.74) | 2264.95 (91.26) |
| 184 | 2216.06 (35.01) | 2117.77 (32.11) | 2313.95 (93.16) |
| 188 | 2257.11 (35.84) | 2160.39 (32.13) | 2362.54 (97.73) |
| 192 | 2299.36 (37.55) | 2201.17 (33.60) | 2409.54 (101.29) |

TABLE 6

| | rotigotine permeation rate [μg/cm²/h] n = 3 (SD) | | |
|---|---|---|---|
| Time [h] | Comparative Example 1 | Comparative Example 2 | Example 1 |
| 0 | 0.00 (0.00) | 0.00 (0.00) | 0.00 (0.00) |
| 4 | 9.32 (1.10) | 5.09 (0.26) | 6.30 (2.16) |
| 8 | 11.30 (0.77) | 7.76 (0.13) | 10.11 (0.28) |
| 12 | 11.58 (1.12) | 9.34 (0.19) | 11.25 (0.10) |
| 16 | 13.77 (1.11) | 10.33 (0.31) | 11.87 (0.15) |
| 20 | 12.80 (0.11) | 10.99 (0.25) | 12.24 (0.10) |
| 24 | 13.00 (0.18) | 11.41 (0.49) | 12.57 (0.19) |
| 28 | 13.14 (0.16) | 11.48 (0.22) | 12.66 (0.38) |
| 32 | 13.24 (0.13) | 11.67 (0.13) | 12.72 (0.24) |
| 36 | 13.28 (0.02) | 11.82 (0.09) | 12.94 (0.21) |
| 40 | 13.21 (0.19) | 11.98 (0.12) | 13.01 (0.17) |
| 44 | 13.15 (0.10) | 12.20 (0.18) | 13.32 (0.29) |
| 48 | 12.87 (0.06) | 12.33 (0.42) | 13.11 (0.43) |
| 52 | 13.35 (0.09) | 12.35 (0.17) | 13.19 (0.59) |
| 56 | 13.37 (0.36) | 12.36 (0.06) | 13.24 (0.35) |
| 60 | 13.26 (0.26) | 12.32 (0.19) | 13.17 (0.23) |
| 64 | 13.15 (0.28) | 12.41 (0.22) | 13.29 (0.26) |
| 68 | 13.03 (0.18) | 12.38 (0.18) | 13.24 (0.38) |
| 72 | 12.96 (0.26) | 12.43 (0.25) | 13.27 (0.48) |
| 76 | 12.67 (0.10) | 12.41 (0.16) | 13.13 (0.79) |
| 80 | 12.88 (0.16) | 12.31 (0.16) | 13.14 (0.40) |
| 84 | 12.93 (0.09) | 12.33 (0.26) | 13.21 (0.41) |
| 88 | 12.53 (0.28) | 12.31 (0.09) | 13.08 (0.42) |
| 92 | 12.27 (0.17) | 12.09 (0.30) | 13.20 (0.53) |
| 96 | 12.36 (0.41) | 12.24 (0.21) | 13.06 (0.72) |
| 100 | 12.43 (0.34) | 12.07 (0.10) | 13.12 (0.55) |
| 104 | 12.34 (0.12) | 12.37 (0.34) | 12.87 (0.57) |
| 108 | 12.16 (0.36) | 12.27 (0.25) | 13.17 (0.67) |
| 112 | 11.45 (0.25) | 12.08 (0.35) | 13.02 (0.55) |
| 116 | 11.40 (0.13) | 11.98 (0.15) | 13.04 (0.68) |

TABLE 6-continued

| | rotigotine permeation rate [μg/cm²/h] n = 3 (SD) | | |
|---|---|---|---|
| Time [h] | Comparative Example 1 | Comparative Example 2 | Example 1 |
| 120 | 11.62 (0.28) | 12.11 (0.51) | 12.92 (0.64) |
| 124 | 11.60 (0.27) | 11.81 (0.23) | 12.56 (0.85) |
| 128 | 11.69 (0.40) | 11.89 (0.07) | 12.90 (0.43) |
| 132 | 11.50 (0.18) | 11.91 (0.27) | 12.86 (0.74) |
| 136 | 11.25 (0.47) | 11.84 (0.38) | 12.73 (0.66) |
| 140 | 11.30 (0.37) | 11.60 (0.18) | 12.70 (0.90) |
| 144 | 11.02 (0.30) | 11.57 (0.34) | 12.51 (0.81) |
| 148 | 11.07 (0.27) | 11.51 (0.59) | 12.55 (0.84) |
| 152 | 11.22 (0.61) | 11.47 (0.33) | 12.48 (0.90) |
| 156 | 11.16 (0.26) | 11.45 (0.36) | 12.63 (0.83) |
| 160 | 10.93 (0.20) | 11.41 (0.54) | 12.31 (0.77) |
| 164 | 10.64 (0.28) | 11.07 (0.44) | 12.51 (1.01) |
| 168 | 11.06 (0.31) | 11.49 (0.28) | 12.37 (0.90) |
| 172 | 10.66 (0.44) | 10.80 (0.24) | 12.29 (1.02) |
| 176 | 10.79 (0.40) | 10.92 (0.14) | 12.05 (0.84) |
| 180 | 10.83 (0.41) | 10.55 (0.17) | 12.31 (1.02) |
| 184 | 10.45 (0.74) | 10.92 (0.35) | 12.25 (0.49) |
| 188 | 10.26 (0.24) | 10.66 (0.33) | 12.15 (1.16) |
| 192 | 10.56 (0.43) | 10.19 (0.42) | 11.75 (0.89) |

TABLE 7

| | rotigotine permeation [μg/cm²] n = 3 (SD) | | |
|---|---|---|---|
| Time [h] | Comparative Example 1 | Example 2a | Example 2b |
| 0 | 0.00 (0.00) | 0.00 (0.00) | 0.00 (0.00) |
| 4 | 28.33 (1.63) | 32.67 (5.59) | 31.38 (6.07) |
| 8 | 69.98 (4.10) | 66.53 (2.86) | 64.20 (3.26) |
| 12 | 119.76 (4.42) | 107.81 (3.43) | 106.58 (3.35) |
| 18 | 196.37 (4.70) | 175.94 (4.69) | 175.12 (5.04) |
| 24 | 274.19 (6.91) | 245.77 (5.03) | 244.82 (4.39) |
| 30 | 351.27 (7.22) | 319.60 (5.94) | 318.08 (5.47) |
| 36 | 458.69 (9.89) | 391.07 (5.75) | 388.44 (4.95) |
| 42 | 541.63 (12.12) | 461.91 (6.45) | 457.21 (4.08) |
| 48 | 622.85 (13.13) | 544.94 (6.38) | 536.06 (5.87) |
| 60 | 782.54 (15.83) | 686.01 (6.08) | 670.37 (4.27) |
| 72 | 932.01 (13.88) | 847.65 (5.93) | 822.16 (5.63) |
| 84 | 1085.37 (18.97) | 990.76 (4.40) | 960.45 (5.67) |
| 96 | 1227.49 (20.78) | 1131.68 (4.40) | 1093.24 (7.87) |
| 108 | 1402.26 (16.07) | 1331.09 (7.54) | 1283.69 (13.00) |
| 120 | 1539.89 (24.08) | 1475.79 (4.44) | 1424.68 (16.27) |
| 132 | 1694.60 (29.54) | 1615.74 (7.32) | 1561.07 (17.43) |
| 144 | 1814.45 (22.97) | 1753.27 (4.46) | 1694.31 (21.70) |
| 156 | 1985.91 (29.33) | 1884.83 (3.34) | 1823.62 (28.92) |
| 168 | 2110.67 (27.74) | 2021.32 (8.81) | 1956.84 (34.06) |
| 180 | 2257.32 (23.93) | 2176.62 (7.34) | 2105.60 (38.84) |
| 192 | 2353.58 (22.00) | 2308.82 (12.34) | 2237.64 (44.95) |

Example 4

In Example 4, the dynamic viscosity of the drug containing adhesive mass of Comparative Example 1, Comparative Example 2, and Example 1 was determined with a Haake Viscotester 2 plus (rotating body no. 1) and a Malvern Kinexus (Couette-bob and cap setup). The results are shown in Table 8 below.

TABLE 8

| dynamic viscosity of the drug containing adhesive mass [dPas (10 s⁻¹)] | | |
|---|---|---|
| Comparative Example 1 | Comparative Example 2 | Example 1 |
| 31.3 | 33.2 | 21.0 |

The lower dynamic viscosity of the drug containing adhesive mass of Example 1 in comparison to Comparative Examples 1 and 2 results in a better processability and thus in a more convenient coating procedure.

Example 5

The composition of the rotigotine-containing biphasic coating mixture is summarized in Table 9 below.

TABLE 9

| Excipients | Solid [%] | Solution [%] |
|---|---|---|
| Ethanol | — | 12.28 |
| Ethyl acetate | — | 3.39 |
| Polyvinylpyrrolidone (Kollidon 90 F) | 4.00 | 2.28 |
| Polyvinylpyrrolidone (Kollidon 30) | 6.00 | 3.42 |
| Sodium metabisulfite solution 10% (w/w) | 0.0045 | 0.03 |
| Ascorbyl palmitate | 0.04 | 0.02 |
| all-rac-Tocopherol | 0.10 | 0.06 |
| Rotigotine | 18.00 | 10.26 |

TABLE 9-continued

| Excipients | Solid [%] | Solution [%] |
|---|---|---|
| BIO PSA 7-4302 (60%) | 35.93 | 34.13 |
| BIO PSA 7-4202 (60%) | 35.93 | 34.13 |
| Total | 100.00 | 100.00 |
| Solids content | | 57% |

Preparation of the Rotigotine-Containing Biphasic Coating Mixture (Step 1):

To a solution of 13.68 g polyvinylpyrrolidone (PVP, Kollidon 90F) and 20.53 g polyvinylpyrrolidone (PVP, Kollidon 30) in 73.67 g ethanol and 20.53 g ethyl acetate, 0.34 g DL-α-tocopherol, 0.14 g ascorbyl palmitate and 0.15 g of an aqueous sodium metabisulfite solution (10% by weight) were added and mixed to obtain a clear solution (1000 rpm, propeller stirrer). 204.81 g silicone adhesive BIO-PSA 7-4202 (60% by weight in ethyl acetate) and 204.81 g silicone adhesive BIO-PSA 7-4302 (60% by weight in ethyl acetate) were added to the obtained PVP solution and stirred at 500 rpm until complete mixing. 61.56 g rotigotine of polymorphic Form II were added while stirring. The mixture was heated up to 40° C. and stirred at 500 rpm for a minimum of 60 min until a homogenous dispersion was obtained.

Preparation of the Transdermal Therapeutic System (TTS) (Step 2):

The mixture obtained in step 1 was coated onto two sheets of a suitable polyester release liner (e.g. Scotchpak™ 9755). The coated release liner sheets were placed in a drying oven and dried at 50° C. for about 30 min and then at 115° C. for about 10 min. The coating thickness was chosen such that removal of the solvents results in a coating weight of each of the two rotigotine-containing layers of 80-82 g/m². The first rotigotine-containing layer was laminated with (1) a polyester-type backing foil and (2) the second rotigotine-containing layer after removal of the release liner from the surface of the first layer to provide the rotigotine-containing self-adhesive layer structure with a rotigotine-containing biphasic layer having a coating weight of 160-164 g/m². Finally, individual systems (TTS) having a size of 10 cm² were punched out of the rotigotine-containing self-adhesive layer structure and sealed into pouches.

Example 6

The composition of the rotigotine-containing biphasic coating reservoir mixture is identical to Example 5.

The composition of the rotigotine-free skin contact layer is summarized in Table 10 below.

TABLE 10

| Excipients | Solid [%] | Solution [%] |
|---|---|---|
| BIO PSA 7-4302 (60%) | 80.00 | 80.00 |
| BIO PSA 7-4202 (60%) | 20.00 | 20.00 |
| Total | 100.00 | 100.00 |

Preparation of the Rotigotine-Free Adhesive Mixture (Step 1):

80.01 g silicone adhesive BIO-PSA 7-4202 (60% by weight in ethyl acetate) were added to 320.01 g silicone adhesive BIO-PSA 7-4302 (60% by weight in ethyl acetate) and stirred at 500 rpm until complete mixing.

Preparation of the Rotigotine-Free Skin Layer (TTS) (Step 2):

The adhesive mixture obtained in step 1 was coated onto sheets of a suitable polyester release liner (e.g. Scotchpak™ 9755). The coated release liner sheets were placed in a drying oven and dried at 50° C. for about 30 min and then at 115° C. for about 10 min. The coating thickness was chosen such that removal of the solvents results in a coating weight of each of the adhesive layer of 28 g/m².

Preparation of the rotigotine-containing biphasic coating mixture (step 3) is identical to step 1 in Example 5.

Preparation of the Transdermal Therapeutic System (TTS) (Step 4):

The mixture obtained in step 3 was coated onto sheets of a suitable polyester release liner (e.g. Scotchpak™ 9755). The coated release liner sheets were placed in a drying oven and dried at 50° C. for about 30 min and then at 115° C. for about 10 min. The coating thickness was chosen such that removal of the solvents results in a coating weight of the rotigotine-containing layer of 139 g/m². The rotigotine-containing layer was laminated with (1) a polyester-type backing foil and (2) the rotigotine—free skin layer of step 2 to provide the rotigotine-containing self-adhesive layer structure with a rotigotine-containing biphasic layer having a coating weight of 167 g/m². Finally, individual systems (TTS) having a size of 10 cm² were punched out of the rotigotine-containing self-adhesive layer structure and sealed into pouches.

Example 7

The composition of the rotigotine-containing biphasic coating mixture as rotigotine—containing skin contact layer is summarized in Table 11 below.

TABLE 11

| Excipients | Solid [%] | Solution [%] |
|---|---|---|
| Ethanol | — | 7.84 |
| Polyvinylpyrrolidone (Kollidon 90 F) | 3.33 | 1.93 |
| Sodium metabisulfite solution 10% (w/w) | 0.015 | 0.01 |
| Ascorbyl palmitate | 0.02 | 0.01 |
| all-rac-Tocopherol | 0.04 | 0.02 |
| Rotigotine | 7.50 | 4.34 |
| BIO PSA 7-4302 (60%) | 71.29 | 68.68 |
| BIO PSA 7-4202 (60%) | 17.82 | 17.17 |
| Total | 100.00 | 100.00 |
| Solids content | | 57% |

Preparation of the Rotigotine-Containing Biphasic Coating Mixture (Step 1):

To a solution of 3.34 g polyvinylpyrrolidone (PVP, Kollidon 90F) in 13.56 g ethanol, 0.02 g DL-α-tocopherol, 0.04 g ascorbyl palmitate and 0.15 g of an aqueous sodium metabisulfite solution (10% by weight) were added and mixed to obtain a clear solution (1000 rpm, propeller stirrer). 29.70 g silicone adhesive BIO-PSA 7-4202 (60% by weight in ethyl acetate) and 118.80 g silicone adhesive BIO-PSA 7-4302 (60% by weight in ethyl acetate) were added to the obtained PVP solution and stirred at 500 rpm until complete mixing. 7.51 g rotigotine of polymorphic Form II were added while stirring. The mixture was heated up to 40° C. and stirred at 500 rpm for a minimum of 60 min until a homogenous dispersion was obtained.

Preparation of the Transdermal Therapeutic System (TTS) (Step 2):

The mixture obtained in step 1 was coated onto sheets of a suitable polyester release liner (e.g. Scotchpak™ 9755). The coated release liner sheets were placed in a drying oven and dried at 50° C. for about 30 min and then at 115° C. for about 10 min. The coating thickness was chosen such that removal of the solvents results in a coating weight of each of the rotigotine-containing layer of 28 g/m². The rotigotine-containing layer was laminated with (1) a polyester-type backing foil and (2) the rotigotine-containing layer of Example 6 with a coating weight of 160-164 g/m² after removal of the release liner from the surface of the first layer to provide the rotigotine-containing self-adhesive layer structure with a rotigotine-containing biphasic layer having a total coating weight of 188-192 g/m². Finally, individual systems (TTS) having a size of 10 cm² were punched out of the rotigotine-containing self-adhesive layer structure and sealed into pouches.

Example 8

Figure 5:
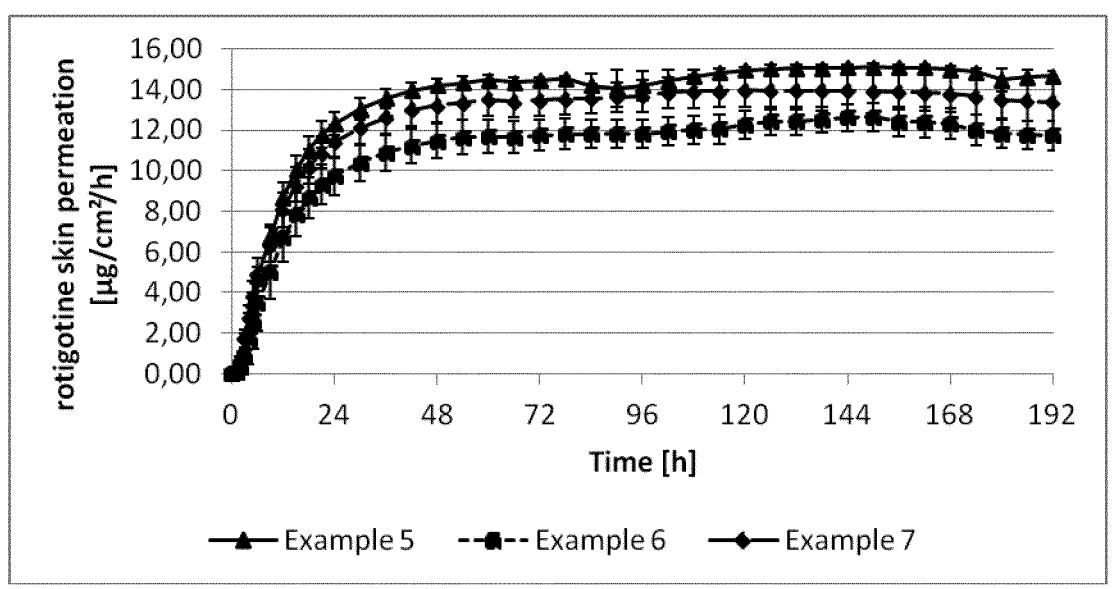
FIG. 5 depicts the rotigotine skin permeation rate of Examples 5, 6 and 7.

In Example 8, the in-vitro skin permeation of Examples 5, 6 and 7 was evaluated by an in-vitro skin permeation test performed over 192 hours using dermatomized human skin of about 300 μm thickness in a flow cell setup. A phosphate buffered saline (PBS) pH 6.2 was used as acceptor medium (32° C.) and the area of the acceptor cells was 0.52 cm². Samples were taken every hour for the first 6 hours, every 3 hours until 18 hours and every 6 hours for the remaining time of the experiments. The permeation of rotigotine into the acceptor medium was determined by HPLC. The results are shown in Tables 12 and 13 and FIG. 5.

TABLE 12

| | rotigotine skin permeation [μg/cm²] n = 3 (SD) | | |
|---|---|---|---|
| Time [h] | Example 5 | Example 6 | Example 7 |
| 0 | 0.00 (0.00) | 0.00 (0.00) | 0.00 (0.00) |
| 1 | 0.08 (0.06) | 0.11 (0.02) | 0.12 (0.01) |
| 2 | 0.40 (0.07) | 0.43 (0.15) | 0.77 (0.56) |
| 3 | 1.57 (0.16) | 1.35 (0.60) | 2.48 (1.61) |
| 4 | 3.95 (0.38) | 3.08 (1.24) | 5.24 (2.89) |
| 5 | 7.57 (0.73) | 5.69 (1.98) | 9.04 (4.28) |
| 6 | 12.36 (1.20) | 9.18 (2.79) | 13.91 (5.69) |
| 9 | 32.46 (3.07) | 24.19 (5.30) | 32.94 (9.63) |
| 12 | 58.53 (5.22) | 44.27 (7.71) | 57.17 (13.11) |
| 15 | 88.64 (7.35) | 67.75 (10.09) | 85.12 (16.34) |
| 18 | 121.66 (9.38) | 93.70 (12.50) | 115.73 (19.40) |
| 21 | 156.98 (11.35) | 121.63 (14.84) | 148.41 (22.29) |
| 24 | 193.94 (13.04) | 150.86 (17.22) | 182.68 (25.08) |
| 30 | 272.15 (16.19) | 213.11 (22.01) | 255.45 (30.34) |
| 36 | 353.62 (18.88) | 278.34 (26.84) | 331.15 (35.72) |
| 42 | 437.33 (21.09) | 345.64 (31.65) | 409.14 (40.97) |
| 48 | 522.53 (22.85) | 414.33 (36.44) | 488.38 (46.06) |
| 54 | 608.55 (24.49) | 484.11 (41.37) | 568.40 (51.16) |
| 60 | 695.40 (25.73) | 554.21 (46.28) | 649.42 (56.18) |
| 66 | 781.61 (26.99) | 624.16 (50.92) | 729.93 (60.86) |
| 72 | 868.28 (28.02) | 694.63 (55.52) | 810.85 (65.41) |
| 78 | 955.51 (28.77) | 765.50 (60.06) | 892.13 (69.80) |
| 84 | 1040.63 (30.06) | 836.39 (64.27) | 973.52 (74.00) |
| 90 | 1124.99 (32.68) | 907.33 (68.39) | 1055.32 (78.31) |
| 96 | 1210.24 (35.12) | 978.08 (72.67) | 1137.45 (82.47) |
| 102 | 1296.73 (37.18) | 1049.66 (76.80) | 1220.56 (86.66) |
| 108 | 1384.60 (38.69) | 1121.75 (81.20) | 1303.98 (90.84) |
| 114 | 1473.52 (39.81) | 1194.00 (85.44) | 1387.47 (95.07) |
| 120 | 1563.25 (40.67) | 1267.62 (90.44) | 1471.27 (99.28) |
| 126 | 1653.44 (41.87) | 1342.30 (95.93) | 1554.91 (103.32) |
| 132 | 1743.80 (42.84) | 1416.98 (101.50) | 1638.61 (107.32) |
| 138 | 1834.18 (43.78) | 1492.10 (107.37) | 1722.20 (111.18) |
| 144 | 1924.70 (44.69) | 1567.82 (113.79) | 1805.90 (115.12) |

TABLE 12-continued

| | rotigotine skin permeation [μg/cm²] n = 3 (SD) | | |
|---|---|---|---|
| Time [h] | Example 5 | Example 6 | Example 7 |
| 150 | 2015.42 (45.48) | 1643.71 (120.18) | 1889.45 (119.23) |
| 156 | 2106.00 (46.33) | 1718.18 (125.54) | 1972.81 (123.60) |
| 162 | 2196.52 (47.00) | 1792.63 (130.85) | 2055.97 (128.00) |
| 168 | 2286.50 (47.82) | 1866.46 (136.22) | 2138.73 (132.36) |
| 174 | 2375.57 (48.91) | 1938.38 (140.51) | 2220.66 (136.65) |
| 180 | 2462.37 (51.96) | 2009.42 (144.89) | 2301.77 (140.58) |
| 186 | 2549.97 (54.03) | 2079.95 (149.31) | 2382.35 (144.54) |
| 192 | 2637.99 (55.34) | 2150.31 (153.14) | 2462.66 (148.56) |

TABLE 13

| | rotigotine skin permeation rate [μg/cm²/h] n = 3 (SD) | | |
|---|---|---|---|
| Time [h] | Example 5 | Example 6 | Example 7 |
| 0 | 0.00 (0.00) | 0.00 (0.00) | 0.00 (0.00) |
| 1 | 0.09 (0.06) | 0.11 (0.02) | 0.14 (0.03) |
| 2 | 0.32 (0.03) | 0.32 (0.17) | 0.66 (0.55) |
| 3 | 1.17 (0.09) | 0.92 (0.46) | 1.70 (1.05) |
| 4 | 2.38 (0.22) | 1.73 (0.63) | 2.76 (1.28) |
| 5 | 3.61 (0.35) | 2.61 (0.74) | 3.80 (1.39) |
| 6 | 4.79 (0.47) | 3.48 (0.81) | 4.86 (1.41) |
| 9 | 6.70 (0.62) | 5.00 (0.85) | 6.34 (1.31) |
| 12 | 8.69 (0.72) | 6.69 (0.84) | 8.08 (1.16) |
| 15 | 10.04 (0.71) | 7.83 (0.83) | 9.32 (1.08) |
| 18 | 11.00 (0.68) | 8.65 (0.84) | 10.20 (1.02) |
| 21 | 11.77 (0.67) | 9.31 (0.81) | 10.89 (0.96) |
| 24 | 12.32 (0.57) | 9.74 (0.81) | 11.42 (0.93) |
| 30 | 13.04 (0.54) | 10.37 (0.81) | 12.13 (0.88) |
| 36 | 13.58 (0.47) | 10.87 (0.81) | 12.62 (0.90) |
| 42 | 13.95 (0.39) | 11.22 (0.81) | 13.00 (0.88) |
| 48 | 14.20 (0.31) | 11.45 (0.80) | 13.21 (0.85) |
| 54 | 14.34 (0.29) | 11.63 (0.82) | 13.34 (0.85) |
| 60 | 14.47 (0.22) | 11.68 (0.82) | 13.50 (0.84) |
| 66 | 14.37 (0.21) | 11.66 (0.78) | 13.42 (0.78) |
| 72 | 14.44 (0.17) | 11.74 (0.78) | 13.49 (0.76) |
| 78 | 14.54 (0.13) | 11.81 (0.78) | 13.55 (0.73) |
| 84 | 14.19 (0.62) | 11.81 (0.73) | 13.56 (0.70) |
| 90 | 14.06 (0.92) | 11.82 (0.73) | 13.63 (0.72) |
| 96 | 14.21 (0.73) | 11.79 (0.78) | 13.69 (0.69) |
| 102 | 14.42 (0.57) | 11.93 (0.77) | 13.85 (0.70) |
| 108 | 14.64 (0.33) | 12.02 (0.82) | 13.90 (0.70) |
| 114 | 14.82 (0.20) | 12.04 (0.80) | 13.92 (0.71) |
| 120 | 14.95 (0.15) | 12.27 (0.84) | 13.97 (0.70) |
| 126 | 15.03 (0.20) | 12.45 (0.92) | 13.94 (0.68) |
| 132 | 15.06 (0.16) | 12.45 (0.94) | 13.95 (0.67) |
| 138 | 15.06 (0.16) | 12.52 (1.00) | 13.93 (0.65) |
| 144 | 15.09 (0.15) | 12.62 (1.09) | 13.95 (0.67) |
| 150 | 15.12 (0.14) | 12.65 (1.08) | 13.92 (0.70) |
| 156 | 15.10 (0.15) | 12.41 (0.90) | 13.89 (0.74) |
| 162 | 15.09 (0.12) | 12.41 (0.89) | 13.86 (0.75) |
| 168 | 15.00 (0.14) | 12.31 (0.90) | 13.79 (0.75) |
| 174 | 14.85 (0.18) | 11.99 (0.88) | 13.66 (0.75) |
| 180 | 14.47 (0.54) | 11.84 (0.95) | 13.52 (0.70) |
| 186 | 14.60 (0.35) | 11.75 (0.98) | 13.43 (0.71) |
| 192 | 14.67 (0.22) | 11.73 (0.91) | 13.39 (0.73) |

The invention relates in particular to the following further items:

1. Transdermal therapeutic system for the transdermal administration of rotigotine containing an therapeutically effective amount of rotigotine base in a self-adhesive layer structure, comprising
   A) a backing layer, and
   B) a rotigotine-containing biphasic layer, the biphasic layer having
      a) an outer phase having a composition comprising 75% to 100% of a polymer or a polymer mixture, and
      b) an inner phase having a composition comprising rotigotine base, wherein the inner phase forms dispersed deposits in the outer phase, and
wherein the inner phase comprises
  i. rotigotine base, and
  ii. a polymer mixture comprising at least two hydrophilic polymers selected from at least two of the polymer groups:
     polyvinylpyrrolidones having a K-Value of at least 80, or from 80 to 200,
     polyvinylpyrrolidones having a K-Value of less than 80, or from 10 to 79,
     copolymers of vinyl caprolactam, vinylacetate and ethylene glycol,
     copolymers of vinylpyrrolidone and vinylacetate,
     copolymers of ethylene and vinylacetate,
     polyethylene glycols,
     polypropylene glycols,
     acrylic polymers,
     modified celluloses,
     wherein the polymer mixture in the inner phase is present in an amount sufficient so that said rotigotine base forms a solid solution with the polymer mixture in the inner phase,
and
  C) optionally an additional skin contact layer.

2. Transdermal therapeutic system in accordance with item 1, wherein the composition of said outer phase is a pressure-sensitive adhesive composition.

3. Transdermal therapeutic system in accordance with item 1 or 2, wherein said polymer or polymer mixture in the outer phase is a/are hydrophobic polymer(s).

4. Transdermal therapeutic system in accordance with any one of items 1 to 3, wherein said polymer or polymer mixture in the outer phase is a/are pressure-sensitive adhesive polymer(s) selected from the group of polysiloxanes, polyisobutylenes, polyacrylates, copolymers of styrene and butadiene, copolymers of styrene and isoprene.

5. Transdermal therapeutic system in accordance with any one of items 1 to 4, wherein said polymer or polymer mixture in the outer phase is a/are pressure-sensitive adhesive polymer(s) selected from the group of polysiloxanes, or polyisobutylenes.

6. Transdermal therapeutic system in accordance with any one of items 1 to 5, wherein said polymer or polymer mixture in the outer phase is a/are pressure-sensitive adhesive polysiloxane(s).

7. Transdermal therapeutic system in accordance with item 6, wherein the polysiloxane(s) is/are amine-resistant.

8. Transdermal therapeutic system in accordance with item 6, wherein the polysiloxane(s) is/are amine-resistant being a product of the condensation reaction of silanol endblocked polydimethylsiloxane with a silica resin and the residual silanol functionality being capped with trimethylsiloxy groups.

9. Transdermal therapeutic system in accordance with any one of items 1 to 8, wherein for the production of the biphasic layer and optionally the skin contact layer a pressure-sensitive adhesive mixture of pressure-sensitive adhesive polysiloxane(s) in heptane is used.

10. Transdermal therapeutic system in accordance with item 9, wherein the pressure-sensitive adhesive mixture is characterized by a solution viscosity at 25° C. and 60% solids content in heptane of more than 150 mPa s.

11. Transdermal therapeutic system in accordance with item 9, wherein the pressure-sensitive adhesive mixture is characterized by a solution viscosity at 25° C. and 60% solids content in heptane of from about 200 mPa s to about 700 mPa s.

12. Transdermal therapeutic system in accordance with item 9, wherein the pressure-sensitive adhesive mixture is characterized by a solution viscosity at 25° C. and 60% solids content in heptane of from about 350 mPa s to about 600 mPa s.

13. Transdermal therapeutic system in accordance with any one of items 1 to 8, wherein for the production of the biphasic layer and optionally the skin contact layer a pressure-sensitive adhesive mixture of pressure-sensitive adhesive polysiloxane(s) in ethyl acetate is used.

14. Transdermal therapeutic system in accordance with item 13, wherein the pressure-sensitive adhesive mixture is characterized by a solution viscosity at 25° C. and 60% solids content in ethyl acetate of more than 350 mPa s.

15. Transdermal therapeutic system in accordance with item 13, wherein the pressure-sensitive adhesive mixture is characterized by a solution viscosity at 25° C. and 60% solids content in ethyl acetate of from about 400 mPa s to about 1500 mPa s.

16. Transdermal therapeutic system in accordance with item 13, wherein the pressure-sensitive adhesive mixture is characterized by a solution viscosity at 25° C. and 60% solids content in ethyl acetate of from about 600 mPa s to about 1300 mPa s.

17. Transdermal therapeutic system in accordance with any one of items 9 to 16, wherein the pressure-sensitive adhesive mixture is characterized by a complex viscosity at 0.01 rad/s at 30° C. of less than $1\times10^9$ Poise.

18. Transdermal therapeutic system in accordance with any one of items 9 to 16, wherein the pressure-sensitive adhesive mixture is characterized by a complex viscosity at 0.01 rad/s at 30° C. of from about $1\times10^5$ to about $9\times10^8$ Poise.

19. Transdermal therapeutic system in accordance with any one of items 1 to 9, wherein for the production of the biphasic layer and optionally the skin contact layer a pressure-sensitive adhesive mixture of a pressure-sensitive adhesive polysiloxane in heptane characterized by a solution viscosity at 25° C. and about 60% solids content in heptane of 500 mPa s and a pressure-sensitive adhesive polysiloxane in heptane characterized by a solution viscosity at 25° C. and about 60% solids content in heptane of 450 mPa s is used.

20. Transdermal therapeutic system in accordance with any one of items 1 to 8 and 13, wherein for the production of the biphasic layer and optionally the skin contact layer a pressure-sensitive adhesive mixture of a pressure-sensitive adhesive polysiloxane in ethyl acetate characterized by a solution viscosity at 25° C. and about 60% solids content in ethyl acetate of 1200 mPa s and a pressure-sensitive adhesive polysiloxane in ethyl acetate characterized by a solution viscosity at 25° C. and about 60% solids content in ethyl acetate of 800 mPa s is used.

21. Transdermal therapeutic system in accordance with any one of items 1 to 20, wherein the polymer mixture in the inner phase comprises two hydrophilic polymers in a ratio of 1:1 to about 1:10.

22. Transdermal therapeutic system in accordance with any one of items 1 to 20, wherein the polymer mixture in the inner phase comprises two hydrophilic polymers in a ratio of 1:1 to about 1:4.

23. Transdermal therapeutic system in accordance with any one of items 1 to 20, wherein the polymer mixture in the inner phase comprises two hydrophilic polymers in a ratio of 1:1 to about 1:2.

24. Transdermal therapeutic system in accordance with any one of items 1 to 23, wherein the at least two hydrophilic polymers are selected from at least two of the polymer groups:
  polyvinylpyrrolidones having a K-Value of at least 80, or from 80 to 200,
  polyvinylpyrrolidones having a K-Value of less than 80, or from 10 to 79,
  copolymers of vinyl caprolactam, vinylacetate and ethylene glycol,
  copolymers of vinylpyrrolidone and vinylacetate,
  copolymers of ethylene and vinylacetate,
  polyethylene glycols,
  polypropylene glycols,
  copolymers of dimethylaminoethyl methacrylate, butyl methacrylate and methyl methacrylat,
  copolymers of methacrylic acid and methyl methacrylat,
  hydroxypropyl methylcellulose, hydroxypropyl methylcellulose acetate succinates.

25. Transdermal therapeutic system in accordance with any one of items 1 to 24, wherein the polymer mixture in the inner phase comprises a polyvinylpyrrolidone having a K-Value of at least 80, or from 80 to 200.

26. Transdermal therapeutic system in accordance with any one of items 1 to 25, wherein the polymer mixture in the inner phase comprises polyvinylpyrrolidone having a K-Value of at least 80, or from 80 to 200, in particular 90, and polyvinylpyrrolidone having a K-Value of less than 80, or from 10 to 79, in particular 30.

27. Transdermal therapeutic system in accordance with item 26, wherein the ratio of polyvinylpyrrolidone having a K-Value of at least 80, or from 80 to 200, to polyvinylpyrrolidone having a K-Value of less than 80, or from 10 to 79, is 4:1 to 1:4.

28. Transdermal therapeutic system in accordance with item 26 or 27, wherein the ratio of polyvinylpyrrolidone having a K-Value of at least 80, or from 80 to 200, to polyvinylpyrrolidone having a K-Value of less than 80, or from 10 to 79, is 2:1 to 1:2.

29. Transdermal therapeutic system in accordance with any one of items 26 to 28, wherein the ratio of polyvinylpyrrolidone having a K-Value of at least 80, or from 80 to 200, to polyvinylpyrrolidone having a K-Value of less than 80, or from 10 to 79, is 1:1 to 1:2.

30. Transdermal therapeutic system in accordance with any one of items 1 to 29, wherein the polymer mixture in the inner phase comprises at least polyvinylpyrrolidone having a K-Value of at least 80, or from 80 to 200, which is present in the same or in a smaller amount than the at least one further hydrophilic polymer.

31. Transdermal therapeutic system in accordance with any one of items 25 to 30, wherein polyvinylpyrrolidone having a K-Value of at least 80, or from 80 to 200, is present in said biphasic layer in an amount of about 0.1 mg/cm$^2$ to about 5 mg/cm$^2$.

32. Transdermal therapeutic system in accordance with any one of items 25 to 30, wherein polyvinylpyrrolidone having a K-Value of at least 80, or from 80 to 200, is present in said biphasic layer in an amount of about 0.1 mg/cm$^2$ to about 1.5 mg/cm$^2$.

33. Transdermal therapeutic system in accordance with any one of items 25 to 32, wherein polyvinylpyrrolidone having a K-Value of at least 80, or from 80 to 200, is present in said biphasic layer in an amount of about 0.5 mg/cm$^2$ to about 0.7 mg/cm$^2$.

34. Transdermal therapeutic system in accordance with any one of items 25 to 33, wherein polyvinylpyrrolidone having a K-Value of at least 80, or from 80 to 200, is present in an amount of about 1% to about 20% of said biphasic layer.

35. Transdermal therapeutic system in accordance with any one of items 25 to 34, wherein polyvinylpyrrolidone having a K-Value of at least 80, or from 80 to 200, is present in an amount of about 1% to about 10% of said biphasic layer.

36. Transdermal therapeutic system in accordance with any one of items 25 to 35, wherein polyvinylpyrrolidone having a K-Value of at least 80, or from 80 to 200, is present in an amount of about 3% to about 5% of said biphasic layer.

37. Transdermal therapeutic system in accordance with any one of items 26 to 36, wherein polyvinylpyrrolidone having a K-Value of less than 80, or from 10 to 79, is present in said biphasic layer in an amount of about 0.1 mg/cm$^2$ to about 5 mg/cm$^2$.

38. Transdermal therapeutic system in accordance with any one of items 26 to 37, wherein polyvinylpyrrolidone having a K-Value of less than 80, or from 10 to 79, is present in said biphasic layer in an amount of about 0.1 mg/cm$^2$ to about 1.5 mg/cm$^2$.

39. Transdermal therapeutic system in accordance with any one of items 26 to 38, wherein polyvinylpyrrolidone having a K-Value of less than 80, or from 10 to 79, is present in said biphasic layer in an amount of about 0.5 mg/cm$^2$ to about 1.0 mg/cm$^2$.

40. Transdermal therapeutic system in accordance with any one of items 26 to 39, wherein polyvinylpyrrolidone having a K-Value of less than 80, or from 10 to 79, is present in an amount of about 1% to about 20% of said biphasic layer.

41. Transdermal therapeutic system in accordance with any one of items 26 to 40, wherein polyvinylpyrrolidone having a K-Value of at less than 80, or from 10 to 79, is present in an amount of about 1% to about 10% of said biphasic layer.

42. Transdermal therapeutic system in accordance with any one of items 26 to 41, wherein polyvinylpyrrolidone having a K-Value of less than 80, or from 10 to 79, is present in an amount of about 5% to about 7% of said biphasic layer.

43. Transdermal therapeutic system in accordance with any one of items 26 to 42, wherein polyvinylpyrrolidone having a K-Value of at least 80, or from 80 to 200, is present in an amount of about 0.5 mg/cm$^2$ to about 0.7 mg/cm$^2$ and polyvinylpyrrolidone having a K-Value of less than 80, or from 10 to 79 is present in an amount of about 0.5 mg/cm$^2$ to about 1.0 mg/cm$^2$.

44. Transdermal therapeutic system in accordance with any one of items 26 to 43, wherein the polyvinylpyrrolidone having a K-Value of less than 80, or from 10 to 79, is a polyvinylpyrrolidone having a K-Value range of 25 to 35, or a nominal K-Value of 30.

45. Transdermal therapeutic system in accordance with any one of items 26 to 44, wherein the polyvinylpyrrolidone having a K-Value of less than 80, or from 10 to 79, is a polyvinylpyrrolidone having a K-Value of less than 25, or a nominal K-Value of 17, or a nominal K-Value of 12.

46. Transdermal therapeutic system in accordance with any one of items 26 to 45, wherein the polyvinylpyrrolidone having a K-Value of at least 80, or from 80 to 200, is a polyvinylpyrrolidone having a K-Value range of 85 to 95, or a nominal K-Value of 90.

47. Transdermal therapeutic system in accordance with any one of items 26 to 46, wherein the polymer mixture in the inner phase comprises polyvinylpyrrolidone having a nominal K-Value of 90 and polyvinylpyrrolidone having a nominal K-Value of 30.

48. Transdermal therapeutic system in accordance with any one of items 26 to 47, wherein the ratio of polyvinylpyrrolidone having a nominal K-Value of 90 and polyvinylpyrrolidone having a nominal K-Value of 30 is 1:1.4, or 1:1.5.

49. Transdermal therapeutic system in accordance with any one of items 1 to 48, wherein the ratio of rotigotine base to the polymer mixture in the inner phase is 1:0.2 to 1:1.

50. Transdermal therapeutic system in accordance with any one of items 1 to 49, wherein the ratio of rotigotine base to the polymer mixture in the inner phase is 1:0.2 to 1:0.8.

51. Transdermal therapeutic system in accordance with any one of items 1 to 50, wherein the ratio of rotigotine base to the polymer mixture in the inner phase is 1:0.4 to 1:0.6.

52. Transdermal therapeutic system in accordance with any one of items 25 to 51, wherein the ratio of rotigotine base to polyvinylpyrrolidone having a K-Value of at least 80, or from 80 to 200, is 1:0.1 to 1:0.5.

53. Transdermal therapeutic system in accordance with any one of items 25 to 52, wherein the ratio of rotigotine base to polyvinylpyrrolidone having a K-Value of at least 80, or from 80 to 200, is 1:0.1 to 1:0.3.

54. Transdermal therapeutic system in accordance with any one of items 25 to 53, wherein the ratio of rotigotine base to polyvinylpyrrolidone having a K-Value of less than 80, or from 10 to 79 is 1:0.1 to 1:0.5

55. Transdermal therapeutic system in accordance with any one of items 25 to 54, wherein the ratio of rotigotine base to polyvinylpyrrolidone having a K-Value of less than 80, or from 10 to 79 is 1:0.2 to 1:0.4.

56. Transdermal therapeutic system in accordance with any one of items 1 to 55, wherein the ratio of rotigotine base to polyvinylpyrrolidone having a K-Value of at least 80, or from 80 to 200, and polyvinylpyrrolidone having a K-Value of less than 80, or from 10 to 79 is about 1:0.2:0.3.

57. Transdermal therapeutic system in accordance with any one of items 1 to 56, wherein polyvinylpyrrolidone having a K-Value of at least 80, or from 80 to 200, is polyvinylpyrrolidone having a nominal K-Value of 90 and polyvinylpyrrolidone having a K-Value of less than 80, or from 10 to 79 is polyvinylpyrrolidone having a nominal K-Value of 30.

58. Transdermal therapeutic system in accordance with any one of items 1 to 57, wherein the transdermal therapeutic system contains 0.1 mg/cm$^2$ to 10.0 mg/cm$^2$ of rotigotine base in said self-adhesive layer structure.

59. Transdermal therapeutic system in accordance with any one of items 1 to 58, wherein the transdermal therapeutic system contains 0.1 mg/cm$^2$ to 5.0 mg/cm$^2$ of rotigotine base in said self-adhesive layer structure.

60. Transdermal therapeutic system in accordance with any one of items 1 to 59, wherein the transdermal therapeutic system contains 0.3 mg/cm$^2$ to 3.0 mg/cm$^2$ of rotigotine base in said self-adhesive layer structure.

61. Transdermal therapeutic system in accordance with any one of items 1 to 60, wherein the transdermal therapeutic system contains 0.3 mg/cm$^2$ to 1.0 mg/cm$^2$ of rotigotine base in said self-adhesive layer structure.

62. Transdermal therapeutic system in accordance with any one of items 1 to 59, wherein the transdermal therapeutic system contains 1.0 mg/cm$^2$ to 1.5 mg/cm$^2$ of rotigotine base in said self-adhesive layer structure.

63. Transdermal therapeutic system in accordance with any one of items 1 to 59, wherein the transdermal therapeutic system contains 1.5 mg/cm$^2$ to 5.0 mg/cm$^2$ of rotigotine base in said self-adhesive layer structure.

64. Transdermal therapeutic system in accordance with any one of items 1 to 59, wherein the transdermal therapeutic system contains 2.0 mg/cm$^2$ to 4.0 mg/cm$^2$, preferably 2.0 mg/cm$^2$ to 3.0 mg/cm$^2$ of rotigotine base in said self-adhesive layer structure.

65. Transdermal therapeutic system in accordance with any one of items 1 to 64, wherein the biphasic layer has an area weight of about 30 g/m$^2$ to about 400 g/m$^2$.

66. Transdermal therapeutic system in accordance with any one of items 1 to 65, wherein the biphasic layer has an area weight of about 30 g/m$^2$ to about 200 g/m$^2$.

67. Transdermal therapeutic system in accordance with any one of items 1 to 66, wherein the biphasic layer has an area weight of about 100 g/m$^2$ to about 200 g/m$^2$.

68. Transdermal therapeutic system in accordance with any one of items 1 to 67, wherein rotigotine base is present in an amount of 1% to 30% of said biphasic layer.

69. Transdermal therapeutic system in accordance with any one of items 1 to 68, wherein rotigotine base is present in an amount of 10% to 26%, preferably of 16% to 26% of said biphasic layer.

70. Transdermal therapeutic system in accordance with any one of items 1 to 69, wherein rotigotine base is present in an amount of 16% to 30% of said biphasic layer.

71. Transdermal therapeutic system in accordance with any one of items 1 to 64, wherein the biphasic layer has an area weight of about 100 g/m$^2$ to about 200 g/m$^2$ and wherein rotigotine base is present in an amount of 16% to 26% of said biphasic layer.

72. Transdermal therapeutic system in accordance with any one of items 1 to 71, wherein the biphasic layer comprises an anti-oxidant selected from the group consisting of sodium metabisulfite, ascorbyl palmitate, tocopherol and esters thereof, ascorbic acid, butylhydroxytoluene, butylhydroxyanisole or propyl gallate.

73. Transdermal therapeutic system in accordance with any one of items 1 to 72, wherein the skin contact layer has a pressure-sensitive adhesive composition comprising pressure-sensitive polymers selected from polysiloxanes, polyisobutylenes, polyacrylates, a copolymer of styrene and butadiene, a copolymer of styrene and isoprene, or a mixture thereof.

74. Transdermal therapeutic system in accordance with any one of items 1 to 73, wherein the skin contact layer has a pressure-sensitive adhesive composition comprising pressure-sensitive adhesive polysiloxane.

75. Transdermal therapeutic system in accordance with any one of items 1 to 74, wherein the skin contact layer is manufactured active agent-free or active agent-containing.

76. Transdermal therapeutic system in accordance with any one of items 1 to 75%, wherein the skin contact layer is manufactured active agent-free and has an area weight of about 5 g/m$^2$ to about 60 g/m$^2$.

77. Transdermal therapeutic system in accordance with any one of items 1 to 76, wherein the skin contact layer is manufactured containing rotigotine base.

78. Transdermal therapeutic system in accordance with item 77, wherein the skin contact layer manufactured containing rotigotine base has an area weight of about 10 g/m$^2$ to about 150 g/m$^2$.

79. Transdermal therapeutic system in accordance with item 77 or 78, wherein the skin contact layer differs from the rotigotine-containing biphasic layer but is also in the form of the rotigotine-containing biphasic layer, the biphasic layer having
a) an outer phase having a composition comprising 75% to 100% of a polymer or a polymer mixture, and
b) an inner phase having a composition comprising rotigotine base,
wherein the inner phase forms dispersed deposits in the outer phase, and
wherein the inner phase comprises
i. rotigotine base, and
ii. at least one hydrophilic polymer,
wherein the at least one hydrophilic polymer in the inner phase is present in an amount sufficient so that said rotigotine base forms a solid solution with the at least one hydrophilic polymer,
optionally wherein the at least one hydrophilic polymer is a polymer mixture comprising at least two hydrophilic polymers,
optionally as defined in items 1 to 30.

80. Transdermal therapeutic system in accordance with any one of items 1 to 79, wherein the skin contact layer comprises in the inner phase polyvinylpyrrolidone having a K-Value of at least 80, or from 80 to 200.

81. Transdermal therapeutic system in accordance with any one of items 1 to 80, wherein the ratio of rotigotine base and polyvinylpyrrolidone having a K-Value of at least 80, or from 80 to 200 in the skin contact layer is from about 1:0.2 to about 1:1.

82. Transdermal therapeutic system in accordance with any one of items 1 to 81, wherein the ratio of rotigotine base and polyvinylpyrrolidone having a K-Value of at least 80, or from 80 to 200 in the skin contact layer is from about 1:0.3 to about 1:0.5.

83. Transdermal therapeutic system in accordance with any one of items 1 to 82, wherein the ratio of rotigotine base to the polymer mixture in the inner phase of the biphasic layer is 1:0.4 to 1:0.6 and the ratio of rotigotine base to polyvinylpyrrolidone having a K-Value of at least 80, or from 80 to 200 in the skin contact layer is 1:0.2 to 1:0.5.

84. Transdermal therapeutic system in accordance with any one of items 1 to 83, wherein rotigotine base is present in the skin contact layer in an amount of 1% to 15% of said skin contact layer.

85. Transdermal therapeutic system in accordance with any one of items 1 to 84, wherein rotigotine base is present in the skin contact layer in an amount of less than 9%, or from 1% to 8% of said skin contact layer.

86. Transdermal therapeutic system in accordance with any one of items 1 to 85, wherein rotigotine base is present in the skin contact layer in a smaller amount than in said biphasic layer.

87. Transdermal therapeutic system in accordance with any one of items 1 to 86, providing a permeation rate of rotigotine base as measured through an EVA membrane in a 4 hours time interval from hour 8 to hour 12 that is therapeutically effective.

88. Transdermal therapeutic system in accordance with any one of items 1 to 87, providing a permeation rate of rotigotine base as measured through an EVA membrane in a 4 hours time interval from hour 8 to hour 12 of at least 10.5 $\mu g/cm^2/hr$ to about 15 $\mu g/cm^2/hr$.

89. Transdermal therapeutic system in accordance with any one of items 1 to 88, providing a permeation rate of rotigotine base as measured through an EVA membrane in a 4 hours time interval from hour 8 to hour 12 of at least 11 $\mu g/cm^2/hr$ to about 15 $\mu g/cm^2/hr$.

90. Transdermal therapeutic system in accordance with any one of items 1 to 89, providing a permeation rate of rotigotine base as measured through an EVA membrane in 4 hours, or 6 hours time intervals from 24 hours to 168 hours that is constant within 20% points from 24 hours to 168 hours.

91. Transdermal therapeutic system in accordance with any one of items 1 to 90, providing a permeation rate of rotigotine base as measured through an EVA membrane in 4 hours, or 6 hours time intervals from 24 hours to 168 hours that is constant within 15% points from 24 hours to 168 hours.

92. Transdermal therapeutic system in accordance with any one of items 1 to 91, providing a permeation rate of rotigotine base as measured through an EVA membrane in 4 hours, or 6 hours time intervals from 24 hours to 168 hours that is constant within 10% points from 24 hours to 168 hours.

93. Transdermal therapeutic system in accordance with any one of items 1 to 92, wherein therapeutically effective amounts of rotigotine base are provided for 1 to 7 days by said transdermal therapeutic system during an administration period to the skin of the patient of 1 to 7 days.

94. Transdermal therapeutic system in accordance with any one of items 1 to 93, wherein therapeutically effective amounts of rotigotine base are provided for 3 days by said transdermal therapeutic system during an administration period to the skin of the patient of 3 days.

95. Transdermal therapeutic system in accordance with any one of items 1 to 94, wherein therapeutically effective amounts of rotigotine base are provided for 4 days by said transdermal therapeutic system during an administration period to the skin of the patient of 4 days.

96. Transdermal therapeutic system in accordance with any one of items 1 to 95, wherein therapeutically effective amounts of rotigotine base are provided for 7 days by said transdermal therapeutic system during an administration period to the skin of the patient of 7 days.

97. Transdermal therapeutic system in accordance with any one of items 1 to 96, wherein the biphasic layer is a dried biphasic layer.

98. Transdermal therapeutic system in accordance with any one of items 1 to 97 for use in a method of treatment.

99. Transdermal therapeutic system in accordance with any one of items 1 to 98, for use in a method of treating patients suffering from Parkinson's disease, Parkinson's plus syndrome, depression, anxiety, AHDS, fibromyalgia, the restless-legs syndrome and for use in the treatment or prevention of dopaminergic neuron loss or the treatment or prevention of cognitive disorders, dementia or lewy body disease.

100. Transdermal therapeutic system for use in accordance with item 98 or 99 by applying a transdermal therapeutic system for at least 24 hours on the skin of a human patient.

101. Transdermal therapeutic system for use in accordance with item 98 or 99 by applying a transdermal therapeutic system for about 96 hours on the skin of a human patient.

102. Transdermal therapeutic system for use in accordance with item 98 or 99 by applying a transdermal therapeutic system for about 168 hours on the skin of a human patient.

103. Method of treatment by applying a transdermal therapeutic system in accordance with any one of items 1 to 99 for at least 24 hours on the skin of a human patient.

104. Method of treatment by applying a transdermal therapeutic system in accordance with any one of items 1 to 99 for about 96 hours on the skin of a human patient.

105. Method of treatment by applying a transdermal therapeutic system in accordance with any one of items 1 to 99 for about 168 hours on the skin of a human patient.

106. Method of treating patients suffering from Parkinson's disease, Parkinson's plus syndrome, depression, anxiety, AHDS, fibromyalgia, the restless-legs syndrome and for use in the treatment or prevention of dopaminergic neuron loss or the treatment or prevention of cognitive disorders, dementia or lewy body disease in accordance with any one of items 104 to 105.

107. Use of a polymer mixture of polyvinylpyrrolidone having a K-Value of at least 80, or from 80 to 200, and polyvinylpyrrolidone having a K-Value of less than 80, or from 10 to 79, in the manufacture of a transdermal therapeutic system for the transdermal administration of rotigotine to provide dispersed solid solution deposits of the polymer mixture including rotigotine base in a pressure-sensitive adhesive composition comprising pressure-sensitive adhesive polysiloxane(s) to control the release of rotigotine base.

108. Method of manufacture of a transdermal therapeutic system for the transdermal administration of rotigotine in accordance with any one of items 1 to 102, comprising the steps of:
  (1) preparing a rotigotine-containing biphasic coating mixture having an inner phase dispersed in an outer phase,
  (2) coating said rotigotine-containing biphasic coating mixture on a film in an amount to provide a layer with a coating weight,
  (3) drying said coated layer to provide a dried layer with a coating weight to provide a rotigotine-containing dried biphasic layer with the desired area weight,
  (4) optionally laminating two or more of said dried layers to provide a rotigotine-containing dried biphasic layer with the desired area weight,
  (5) laminating said rotigotine-containing dried biphasic layer to a backing layer,
  (6) optionally laminating said rotigotine-containing dried biphasic layer to an additional skin contact layer.

109. Method in accordance with item 108, wherein the preparation of the rotigotine-containing biphasic coating mixture comprises the steps of:
  (1) mixing a polymer mixture comprising at least two hydrophilic polymers selected from at least two of the polymer groups:
    polyvinylpyrrolidones having a K-Value of at least 80, or from 80 to 200,
    polyvinylpyrrolidones having a K-Value of less than 80, or from 10 to 79,
    copolymers of vinyl caprolactam, vinylacetate and ethylene glycol,
    copolymers of vinylpyrrolidone and vinylacetate,
    copolymers of ethylene and vinylacetate,
    polyethylene glycols,
    polypropylene glycols,
    acrylic polymers,
    modified celluloses,
    with a solvent to obtain a solution,
  (2) optionally adding tocopherol, ascorbyl palmitate, and an aqueous sodium metabisulfite solution to the solution of step 1,
  (3) adding rotigotine base and a mixture of a composition comprising 75% to 100% of a polymer or a polymer mixture in a solvent to said solution to provide a rotigotine-containing biphasic coating mixture.

110. Method in accordance with item 108 or 109, wherein said rotigotine-containing biphasic layer is laminated to an additional skin contact layer and wherein the preparation of the skin contact layer comprises the steps of:
  (1) providing an adhesive coating mixture, preferably a rotigotine-containing biphasic coating mixture having an inner phase dispersed in an outer phase and comprising at least one hydrophilic polymer in the inner phase,
  (2) coating said adhesive coating mixture on a film to provide a layer of said adhesive coating mixture,
  (3) drying said coated layer to provide a dried layer with a coating weight to provide said skin contact layer with the desired area weight,
  (4) optionally laminating two or more of said dried layers to provide said skin contact layer with the desired area weight.

111. Method in accordance with items 108 to 110, wherein for the production of the biphasic layer and optionally the additional skin contact layer a pressure-sensitive adhesive mixture of pressure-sensitive adhesive polysiloxanes in heptane or ethyl acetate is used.

112. Transdermal therapeutic system for the transdermal administration of rotigotine containing an therapeutically effective amount of rotigotine base in a self-adhesive layer structure, comprising
  A) a backing layer, and
  B) a rotigotine-containing dried biphasic layer, the dried biphasic layer having
    a) an outer phase having a pressure-sensitive adhesive composition comprising 75% to 100% of pressure sensitive adhesive polysiloxanes, and
    b) an inner phase having a composition comprising rotigotine base,
    wherein the inner phase forms dispersed deposits in the outer phase, and
    wherein the inner phase comprises
      i. 16% to 26% of rotigotine base of said dried biphasic layer, and
      ii. a polymer mixture comprising polyvinylpyrrolidone having a K-Value of at least 80, or from 80 to 200, and polyvinylpyrrolidone having a K-Value of less than 80, or from 10 to 79,
      wherein the polymer mixture in the inner phase is present in an amount sufficient so that said rotigotine base forms a solid solution with the polymer mixture in the inner phase,
    wherein the dried biphasic layer has an area weight of about 100 g/m$^2$ to about 200 g/m$^2$,
  and
  C) optionally an additional skin contact layer.

113. Transdermal therapeutic system for the transdermal administration of rotigotine containing 2.0 mg/cm$^2$ to 3.0 mg/cm$^2$ of rotigotine base in a self-adhesive layer structure, comprising
  A) a backing layer, and
  B) a rotigotine-containing biphasic layer, the biphasic layer having
    a) an outer phase having a pressure-sensitive adhesive composition comprising 75% to 100% of pressure sensitive adhesive polysiloxanes, and
    b) an inner phase having a composition comprising rotigotine base,
    wherein the inner phase forms dispersed deposits in the outer phase, and wherein the inner phase comprises
i. rotigotine base, and
ii. a polymer mixture comprising polyvinylpyrrolidone having a K-Value of at least 80, or from 80 to 200, and polyvinylpyrrolidone having a K-Value of less than 80, or from 10 to 79,
wherein the polymer mixture in the inner phase is present in an amount sufficient so that said rotigotine base forms a solid solution with the polymer mixture in the inner phase,
wherein the ratio of rotigotine base to polyvinylpyrrolidone having a K-Value of less than 80, or from 10 to 79 is 1:0.1 to 1:0.5,
wherein the biphasic layer has an area weight of about 100 g/m² to about 200 g/m²,
and
C) an additional skin contact layer.

114. Transdermal therapeutic system for the transdermal administration of rotigotine containing an therapeutically effective amount of rotigotine base in a self-adhesive layer structure, comprising
A) a backing layer, and
B) a rotigotine-containing biphasic layer, the biphasic layer having
a) an outer phase having a pressure-sensitive adhesive composition comprising 75% to 100% of pressure-sensitive adhesive polysiloxanes, and
b) an inner phase having a composition comprising rotigotine base,
wherein the inner phase forms dispersed deposits in the outer phase, and
wherein the inner phase comprises
i. 16% to 26% of rotigotine base of said biphasic layer, and
ii. a polymer mixture comprising polyvinylpyrrolidone having a K-Value of at least 80, or from 80 to 200, and polyvinylpyrrolidone having a K-Value of less than 80, or from 10 to 79,
wherein the polymer mixture in the inner phase is present in an amount sufficient so that said amount of rotigotine base forms a solid solution with the polymer mixture in the inner phase,
wherein the biphasic layer has an area weight of about 100 g/m² to about 200 g/m²,
and
C) an additional rotigotine-containing skin contact layer which is also in the form of a biphasic layer having
a) an outer phase having a pressure-sensitive adhesive composition comprising 75% to 100% of pressure-sensitive adhesive polysiloxanes, and
b) an inner phase having a composition comprising rotigotine base,
wherein the inner phase forms dispersed deposits in the outer phase, and
wherein the inner phase comprises
i. from 1% to 8% rotigotine base of said skin contact layer, and
ii. polyvinylpyrrolidone having a K-Value of at least 80, or from 80 to 200, wherein said polyvinylpyrrolidone is present in an amount sufficient so that said amount of rotigotine base forms a solid solution with said polyvinylpyrrolidone,
wherein the skin contact layer has an area weight of about 10 g/m² to about 150 g/m².

115. Transdermal therapeutic system for the transdermal administration of rotigotine which provides a permeation rate of rotigotine base
(a) of at least 11 µg/cm²/hr to about 15 µg/cm²/hr as measured through an EVA membrane in a 4 hours time interval from hour 8 to hour 12, and
(b) which is constant within 20% points from 24 hours to 168 hours when measured through an EVA membrane in 4 hours time intervals from 24 hours to 168 hours.

The invention claimed is:
1. A transdermal therapeutic system for the transdermal administration of rotigotine, comprising:
A) a backing layer;
B) a self-adhesive rotigotine-containing biphasic layer; and
C) optionally an additional skin contact layer;
wherein the biphasic layer has:
a) an outer phase having a composition comprising 75% to 100% of a polymer or a polymer mixture that does not include polyacrylates; and
b) an inner phase that forms dispersed deposits in the outer phase;
wherein the inner phase comprises:
i. rotigotine base in an amount ranging from 10% to 30% of said biphasic layer; and
ii. a polymer mixture comprising at least two hydrophilic polymers, including a polyvinylpyrrolidone having a K-Value of at least 80 and a polyvinylpyrrolidone having a K-Value of less than 80, and
wherein the polymer mixture in the inner phase is present in an amount sufficient so that said rotigotine base forms a solid solution with the polymer mixture in the inner phase and the transdermal therapeutic system administers therapeutically effective amounts of rotigotine for at least 3 days, and
the transdermal therapeutic system exhibits a permeation rate of rotigotine base as measured through an EVA membrane in 4-hour or 6-hour time intervals from 24 hours to 168 hours that is constant within 20% points from 24 hours to 168 hours
and the polyvinylpyrrolidone having a K-Value of at least 80 is present in a same or smaller amount than the polyvinylpyrrolidone having a K-Value of less than 80.

2. The transdermal therapeutic system in accordance with claim 1; wherein said polymer or polymer mixture in the outer phase is a hydrophobic polymer or a mixture of hydrophobic polymers, respectively.

3. The transdermal therapeutic system in accordance with claim 1; wherein said polymer or polymer mixture in the outer phase is a pressure-sensitive adhesive polymer or a mixture of pressure-sensitive adhesive polymers, respectively, selected from the group consisting of polysiloxanes, polyisobutylenes, copolymers of styrene and butadiene, and copolymers of styrene and isoprene.

4. The transdermal therapeutic system in accordance with claim 1: wherein said polymer or polymer mixture in the outer phase consists of a pressure-sensitive adhesive polysiloxane or a mixture of pressure-sensitive adhesive polysiloxanes, respectively, and one of the hydrophilic polymers within the inner phase is polyvinylpyrrolidone having a K-value range of 25 to 35.

5. The transdermal therapeutic system in accordance with claim 1; wherein the ratio of rotigotine base to polyvinylpyrrolidone having a K-Value of at least 80 is 1:0.1 to 1:0.5.

6. The transdermal therapeutic system in accordance with claim 1, wherein the ratio of rotigotine base to polyvinylpyrrolidone having a K-Value of less than 80 is 1:0.1 to 1:0.5.

7. The transdermal therapeutic system in accordance with claim 1; wherein the transdermal therapeutic system contains 1.5 mg/cm² to 5 mg/cm² of rotigotine base.

8. The transdermal therapeutic system in accordance with claim 1; wherein the biphasic layer has an area weight of about 30 g/m² to about 200 g/m².

9. The transdermal therapeutic system in accordance with claim 1; wherein rotigotine base is present in an amount of 10% (w/w) to 26% (w/w) of said biphasic layer.

10. The transdermal therapeutic system in accordance with claim 1; wherein the transdermal therapeutic system includes the skin contact layer, which is manufactured active agent-free, and the biphasic layer inner phase comprises two hydrophilic polymers in a polyvinylpyrrolidone having a K-Value of at least 80 to further polymer ratio of 1:1 to about 1:10.

11. The transdermal therapeutic system in accordance with claim 1; wherein the transdermal therapeutic system includes the skin contact layer, which is manufactured containing rotigotine base, and the biphasic layer inner phase comprises two hydrophilic polymers in a polyvinylpyrrolidone having a K-Value of at least 80 and a polyvinylpyrrolidone have a K-Value of less than 80, a ratio of polyvinylpyrrolidone with a K-Value of at least 80 to a polyvinylpyrrolidone with a K-Value less than 80 in a range of 1:1 to about 1:10.

12. The transdermal therapeutic system in accordance with claim 11; wherein the skin contact layer manufactured containing rotigotine base has an area weight of about 10 g/m² to about 150 g/m².

13. The transdermal therapeutic system in accordance with claim 11; wherein the skin contact layer differs from the rotigotine-containing biphasic layer but is also biphasic, wherein the biphasic skin contact layer has:
   a) an outer phase having a composition comprising 75% to 100% of a polymer or a polymer mixture, and
   b) an inner phase that forms dispersed deposits in the outer phase; wherein the inner phase of the skin contact layer comprises:
      i. rotigotine base; and
      ii. one or more polyvinylpyrrolidones, wherein at least one polyvinylpyrrolidone has a K-Value of at least 80; and wherein the at least one polyvinylpyrrolidone with a K-Value of at least 80 in the inner phase of the skin contact layer is present in an amount sufficient so that said rotigotine base forms a solid solution with the at least one hydrophilic polymer.

14. The transdermal therapeutic system in accordance with claim 11; wherein rotigotine base is present in the skin contact layer in an amount of 1% (w/w) to 15% (w/w) of said skin contact layer.

15. The transdermal therapeutic system in accordance with claim 11; wherein rotigotine base is present in the skin contact layer in an amount of less than 9% (w/w) of said skin contact layer, and the inner phase of the skin contact layer comprises hydrophilic polymer consisting of polyvinylpyrrolidone having a K-Value of at least 80.

16. The transdermal therapeutic system in accordance with claim 11; wherein rotigotine base is present in the skin contact layer in a smaller amount than in said biphasic layer.

17. The transdermal therapeutic system in accordance with claim 1; wherein the transdermal therapeutic system provides a permeation rate of rotigotine base as measured through an EVA membrane in a 4-hour time interval from hour 8 to hour 12 that is therapeutically effective.

18. The transdermal therapeutic system in accordance with claim 1; wherein the transdermal therapeutic system provides a permeation rate of rotigotine base as measured through an EVA membrane in a 4-hour time interval from hour 8 to hour 12 of at least 11 µg/cm²/hr to about 15 µg/cm²/hr.

19. The transdermal therapeutic system in accordance with claim 1; wherein the transdermal therapeutic system provides a permeation rate of rotigotine base as measured through an EVA membrane in 4-hour or 6-hour time intervals from 24 hours to 168 hours that is constant within 10% points from 24 hours to 168 hours.

20. The transdermal therapeutic system in accordance with claim 1; wherein the transdermal therapeutic system provides therapeutically effective amounts of rotigotine base for 3 to 7 days during an administration period to skin of a patient of 3 to 7 days.

21. The transdermal therapeutic system in accordance with claim 1; wherein the biphasic layer is a dried biphasic layer.

22. A transdermal therapeutic system for the transdermal administration of rotigotine, comprising:
   A) a backing layer;
   B) a self-adhesive rotigotine-containing dried biphasic layer that contains rotigotine base; and
   C) optionally an additional skin contact layer;
   wherein the dried biphasic layer has:
      a) an outer phase; and
      b) an inner phase that forms dispersed deposits in the outer phase, and wherein the outer phase comprises:
         a pressure-sensitive adhesive composition comprising one or more polymers consisting of pressure sensitive adhesive polysiloxanes;
   wherein the inner phase comprises:
      i. rotigotine in an amount ranging from 16% to 26% of said dried biphasic layer, and
      ii. a polymer mixture comprising polyvinylpyrrolidone having a K-Value of at least 80, and polyvinylpyrrolidone having a K-Value of less than 80, with the polyvinylpyrrolidone having a K-Value of at least 80 present in a same or smaller amount that the polyvinylpyrrolidone having a K-Value of less than 80;
   wherein the polymer mixture in the inner phase is present in an amount sufficient so that said rotigotine base forms a solid solution with the polymer mixture in the inner phase; and
   wherein the dried biphasic layer has an area weight of about 100 g/m² to about 200 g/m²,
   the transdermal therapeutic system administers therapeutically effective amounts of rotigotine for at least 3 days, and
   the transdermal therapeutic system exhibits a permeation rate of rotigotine base as measured through an EVA membrane in 4-hour or 6-hour time intervals from 24 hours to 168 hours that is constant within 20% points from 24 hours to 168 hours.

23. A transdermal therapeutic system for the transdermal administration of rotigotine containing 2.0 mg/cm² to 3.0 mg/cm² of rotigotine base in a self-adhesive layer structure, comprising:
   A) a backing layer; and
   B) a self-adhesive rotigotine-containing biphasic layer;
   C) an additional skin contact layer;
   wherein the biphasic layer has:
      a) an outer phase having a pressure-sensitive adhesive composition comprising polymer consisting of pressure sensitive adhesive polysiloxanes; and b) an inner phase that forms dispersed deposits in the outer phase; wherein
the inner phase comprises:
  i. rotigotine base in an amount ranging from 10% to 30% of said biphasic layer; and
  ii. a polymer mixture comprising polyvinylpyrrolidone having a K-Value of at least 80, and polyvinylpyrrolidone having a K-Value of less than 80, with the polyvinylpyrrolidone having a K-Value of at least 80 present in a same or smaller amount that the polyvinylpyrrolidone having a K-Value of less than 80;
wherein the polymer mixture in the inner phase is present in an amount sufficient so that said rotigotine base forms a solid solution with the polymer mixture in the inner phase;
wherein the ratio of rotigotine base to polyvinylpyrrolidone having a K-Value of less than 80 is 1:0.1 to 1:0.5;
wherein the biphasic layer has an area weight of about 100 g/m$^2$ to about 200 g/m$^2$ and
wherein the transdermal therapeutic system contains 2.0 mg/cm$^2$ to 3.0 mg/cm$^2$ of rotigotine base and the transdermal therapeutic system administers therapeutically effective amounts of rotigotine for at least 3 days,
and the transdermal therapeutic system provides a permeation rate of rotigotine base as measured through an EVA membrane in 4-hour or 6-hour time intervals from 24 hours to 168 hours that is constant within 20% points from 24 hours to 168 hours.

24. A transdermal therapeutic system for the transdermal administration of rotigotine, comprising:
A) a backing layer;
B) a self-adhesive rotigotine-containing biphasic layer that contains rotigotine base; and
C) an additional rotigotine-containing skin contact layer that contains rotigotine base; wherein the biphasic layer has:
  a) an outer phase; and
  b) an inner phase that forms dispersed deposits in the outer phase, and
wherein the outer phase comprises:
  a pressure-sensitive adhesive composition comprising polymer consisting of pressure sensitive adhesive polysiloxanes;
wherein the biphasic layer inner phase comprises:
  i. rotigotine base in an amount ranging from 16% to 26% of said biphasic layer; and
  ii. a polymer mixture comprising polyvinylpyrrolidone having a K-Value of at least 80, and polyvinylpyrrolidone having a K-Value of less than 80, with the polyvinylpyrrolidone having a K-Value of at least 80 present in a same or smaller amount that the polyvinylpyrrolidone having a K-Value of less than 80;
wherein the polymer mixture in the inner phase is present in an amount sufficient so that said rotigotine base of the biphasic layer forms a solid solution with the polymer mixture in the inner phase;
wherein the biphasic layer has an area weight of about 100 g/m$^2$ to about 200 g/m$^2$;
wherein the additional rotigotine-containing skin contact layer is also biphasic and has:
  a) an outer phase; and
  b) an inner phase that forms dispersed deposits in the outer phase, and wherein the outer phase of the skin contact layer comprises:
    a pressure-sensitive adhesive composition comprising 75% to 100% of pressure sensitive adhesive polysiloxanes;
wherein the inner phase of the skin contact layer comprises:
  i. from 1% to 8% rotigotine base; and
  ii. polyvinylpyrrolidone consisting of polyvinylpyrrolidone having a K-Value of at least 80, which is present in an amount sufficient so that said rotigotine base of the skin contact layer forms a solid solution with said polyvinylpyrrolidone,
wherein the skin contact layer has an area weight of about 10 g/m$^2$ to about 150 g/m$^2$ and the transdermal therapeutic system administers therapeutically effective amounts of rotigotine for at least 3 days,
and the transdermal therapeutic system provides a permeation rate of rotigotine base as measured through an EVA membrane in 4-hour or 6-hour time intervals from 24 hours to 168 hours that is constant within 20% points from 24 hours to 168 hours.

25. The transdermal therapeutic system in accordance with claim 1; wherein therapeutically effective amounts of rotigotine base are provided for at least 7 days.

26. A transdermal therapeutic system for rotigotine in accordance with claim 23, said system comprising:
a self-adhesive rotigotine-containing layer that contains rotigotine base,
wherein the transdermal therapeutic system provides a permeation rate of the rotigotine base:
  (a) of at least 11 μg/cm$^2$/hr to about 15 μg/cm$^2$/hr as measured through an EVA membrane in a 4-hour time interval from hour 8 to hour 12; and
  (b) which is constant within 10% points from 24 hours to 168 hours when measured through an EVA membrane in 4-hour time intervals from 24 hours to 168 hours and
  (c) the transdermal therapeutic system administers therapeutically effective amounts of rotigotine for at least 3 days.

27. The transdermal therapeutic system in accordance with claim 1; wherein the polymer mixture in the inner phase comprises polyvinylpyrrolidone having a K-Value of 90 and polyvinylpyrrolidone having a K-Value of 30 and the rotigotine base is delivered in a therapeutically effective amount of at least 11 μg/cm$^2$/hr from 12 to 192 hours.

28. The transdermal therapeutic system in accordance with claim 26; wherein the rotigotine-containing layer is a biphasic layer whose outer phase comprises pressure-sensitive adhesive consisting of pressure-sensitive adhesive polysiloxane(s) and whose inner phase contains a mixture of polyvinylpyrrolidones, one of which has a K-Value of at least 80 and one of which has a K-Value of from 10 to 79, said polyvinylpyrrolidone mixture comprising 8 to 20% of the biphasic layer.

29. The transdermal therapeutic system in accordance with claim 28, wherein the two hydrophilic polymers are polyvinylpyrrolidone having a K-Value of at least 80 and polyvinylpyrrolidone having a K-Value of 25 to 36, present in a ratio ranging from 1:1 to 1:2, and the rotigotine is present in an amount of 16 to 30%.

30. The transdermal therapeutic system in accordance with claim 29, wherein the polyvinylpyrrolidone having a K-Value of at least 80 is present in a smaller amount than the polyvinylpyrrolidone having a K-Value of 25 to 36.

31. The transdermal therapeutic system in accordance with claim 27, wherein the polyvinylpyrrolidone having a K-Value of at least 80 has a nominal K-Value of 90 and the polyvinylpyrrolidone having a K-Value of 25 to 36 has a nominal K-Value of 30, and said system exhibits a higher permeated rotigotine in μg/cm$^2$/h from about 96 hours to 192 hours than comparable systems containing the same amount of rotigotine, and containing either polyvinylpyrrolidone having a nominal K-Value of 90 alone or polyvinylpyrrolidone having a nominal K-Value of 30 alone.

32. The transdermal therapeutic system in accordance with claim 24, wherein the skin contact layer comprises 6.66 to 8% rotigotine base.

33. The transdermal transdermal therapeutic system in accordance with claim 1, wherein the system contains from about 0.3 to 0.4 mg/cm$^2$/day rotigotine base and can administer rotigotine base in therapeutically effective amounts for at least 7 days.

34. The transdermal therapeutic system in accordance with claim 23, wherein the skin contact layer comprises a single hydrophilic polymer, polyvinylpyrrolidone having a K-value of at least 80.

35. The transdermal therapeutic system in accordance with claim 34, wherein the outer phase of the rotigotine-containing biphasic layer comprises pressure-sensitive adhesive consisting of pressure sensitive adhesive polysiloxanes containing a mixture of either
 (a) polysiloxane having a solution viscosity at 25° C. and about 60% solids content in heptane of 500 mPas and
 (b) polysiloxane having a solution viscosity at 25° C. and about 60% solids content in heptane of 450 mPas
 or
 (c) polysiloxane having a solution viscosity at 25° C. and about 60% solids content in ethyl acetate of 1200 mPas and (d) polysiloxane having a solution viscosity at 25° C. and about 60% solids content in ethyl acetate of 800 mPas,
 with the foregoing polysiloxanes present in a ratio of (a) to (b) or (c) to (d) of 50:50 to 30:70.

36. The transdermal therapeutic system in accordance with claim 35, wherein the skin contact layer comprises pressure-sensitive adhesive consisting of pressure sensitive adhesive polysiloxane containing a mixture of either
 (a) a solution viscosity at 25° C. and about 60% solids content in heptane of 500 mPas and (b) a solution viscosity at 25° C. and about 60% solids content in heptane of 450 mPas
 or
 (c) a solution viscosity at 25° C. and about 60% solids content in ethyl acetate of 1200 mPas and (d) a solution viscosity at 25° C. and about 60% solids content in ethyl acetate of 800 mPas,
 wherein (a) is present in a higher amount than (b) and (c) is present in a higher amount than (d).

37. The transdermal therapeutic system in accordance with claim 1; wherein
 (a) the outer phase polymer consists of polysiloxane;
 (b) the inner phase polymer mixture consists of polyvinylpyrrolidones having a K-Value of 90 and polyvinylpyrrolidones having a K-Value of 30;
 (c) the rotigotine is present in an amount of 18% (w/w) of said biphasic layer; and
 the transdermal therapeutic system provides a permeation rate of rotigotine base as measured through an EVA membrane in 4-hour or 6-hour time intervals from 24 hours to 168 hours that is constant within 6.78% points from 24 hours to 168 hours.

38. The transdermal therapeutic system in accordance with claim 1;
 wherein
 (a) the outer phase polymer consists of polysiloxane;
 (b) the inner phase polymer mixture consists of polyvinylpyrrolidones having a K-Value of 90 and polyvinylpyrrolidones having a K-Value of 30;
 (c) the rotigotine is present in an amount of 18% (w/w) of said biphasic layer; and
 the transdermal therapeutic system provides a permeation rate of rotigotine base as measured through dermatomized human skin of about 300 μm thickness in 6-hour time intervals from 24 hours to 168 hours that is constant within 3.88% points from 24 hours to 168 hours.

* * * * *